(12) United States Patent
Grimes et al.

(10) Patent No.: US 7,964,371 B2
(45) Date of Patent: Jun. 21, 2011

(54) GASTRIN HORMONE IMMUNOASSAYS

(75) Inventors: Stephen Grimes, Davis, CA (US); John Little, Cambridgeshire (GB); Lorraine McLoughlin, Cambridgeshire (GB)

(73) Assignee: Cancer Advances, Inc., Durham, NC (US)

(*) Notice: Subject to any disclaimer, the term of this patent is extended or adjusted under 35 U.S.C. 154(b) by 646 days.

(21) Appl. No.: 11/800,889

(22) Filed: May 7, 2007

(65) Prior Publication Data
US 2007/0249005 A1    Oct. 25, 2007

Related U.S. Application Data

(63) Continuation of application No. 10/813,336, filed on Mar. 29, 2004, now Pat. No. 7,235,376.

(60) Provisional application No. 60/458,244, filed on Mar. 28, 2003, provisional application No. 60/557,759, filed on Mar. 29, 2004.

(51) Int. Cl.
  G01N 33/53    (2006.01)
  G01N 33/537   (2006.01)
  G01N 33/543   (2006.01)

(52) U.S. Cl. ............... 435/7.94; 436/530; 500/391.1

(58) Field of Classification Search .............. None
  See application file for complete search history.

(56) References Cited

U.S. PATENT DOCUMENTS

| | | | |
|---|---|---|---|
| 3,931,141 A | 1/1976 | Wissmann | |
| 4,069,313 A | 1/1978 | Woodhour et al. | |
| 4,196,265 A | 4/1980 | Koprowski et al. | 435/2 |
| 4,201,770 A | 5/1980 | Stevens | |
| 4,302,386 A | 11/1981 | Stevens | |
| 4,384,995 A | 5/1983 | Stevens | |
| 4,526,716 A | 7/1985 | Stevens | |
| 4,565,805 A | 1/1986 | Smirnov | |
| 4,687,759 A | 8/1987 | Martinez et al. | |
| 4,691,006 A | 9/1987 | Stevens | |
| 4,713,366 A | 12/1987 | Stevens | |
| 4,762,913 A | 8/1988 | Stevens | |
| 4,767,842 A | 8/1988 | Stevens | |
| 4,794,103 A | 12/1988 | Bertolini | |
| 4,803,170 A | 2/1989 | Stanton et al. | |
| 4,816,567 A | 3/1989 | Cabilly et al. | |
| 4,840,939 A | 6/1989 | Leveen et al. | |
| 4,894,443 A | 1/1990 | Greenfield et al. | |
| 4,923,819 A * | 5/1990 | Fernandez et al. | 436/518 |
| 4,925,922 A | 5/1990 | Byers et al. | |
| 4,971,792 A | 11/1990 | Steplewski et al. | |
| 4,978,683 A | 12/1990 | Rovati et al. | |
| 4,997,950 A | 3/1991 | Murphy et al. | 548/304.1 |
| 5,006,334 A | 4/1991 | Stevens | |
| 5,023,077 A | 6/1991 | Gevas et al. | 424/88 |
| 5,035,988 A | 7/1991 | Nakamura et al. | |
| 5,055,404 A | 10/1991 | Ueda et al. | |
| 5,110,911 A | 5/1992 | Samuel et al. | |
| 5,120,829 A | 6/1992 | Pierschbacher et al. | |
| 5,162,504 A | 11/1992 | Horoszewicz | |
| 5,164,299 A * | 11/1992 | Lambert | 435/7.92 |
| 5,242,799 A | 9/1993 | Samuel et al. | |
| 5,256,542 A | 10/1993 | Chang | |
| 5,319,073 A | 6/1994 | Wank | |
| 5,468,494 A | 11/1995 | Gevas et al. | 424/195.11 |
| 5,484,596 A | 1/1996 | Hanna, Jr. et al. | |
| 5,580,563 A | 12/1996 | Tam et al. | |
| 5,585,474 A | 12/1996 | Iwaki et al. | |
| 5,607,676 A | 3/1997 | Gevas et al. | |
| 5,609,870 A | 3/1997 | Gevas et al. | 424/184.1 |
| 5,622,702 A | 4/1997 | Gevas et al. | 424/184.1 |
| 5,639,613 A | 6/1997 | Shay et al. | |
| 5,643,735 A | 7/1997 | Yokoi et al. | 435/7.9 |
| 5,665,864 A | 9/1997 | Quaranta et al. | |
| 5,665,874 A | 9/1997 | Kuhajda et al. | |
| 5,668,117 A | 9/1997 | Shapiro | |
| 5,683,695 A | 11/1997 | Shen et al. | |
| 5,688,506 A | 11/1997 | Grimes et al. | 424/184.1 |
| 5,698,201 A | 12/1997 | Stevens | |
| 5,703,213 A | 12/1997 | Wands et al. | |
| 5,712,369 A | 1/1998 | Old et al. | |
| 5,723,718 A | 3/1998 | Berens | |
| 5,731,159 A | 3/1998 | Waldman | |

(Continued)

FOREIGN PATENT DOCUMENTS
EP    0380230    8/1990

(Continued)

OTHER PUBLICATIONS

Harlow, E. and Lane, D., Antibodies: A Laboratory Manual (1988) Cold Spring Harbor Laboratory Press, Cold Spring Harbor, NY, pp. 555-556, 559, 561, 578-581, and 591-593.*

Masseyef et al. "The Art of Assay Design in Heterologous Enzyme Immunoassay", Immunoenzymatic Techniques, pp. 139-155, Mar. 16-18, 1983.*

Fornai et al. "Cholecystokinin CCK2 receptors mediate the peptide's inhibitory actions on the contractile activity of human distal colon via the nitric oxide pathway" British Journal of Pharmacology (2007) 151, 1246-1253.*

Sugano et al., The Journal of Biological Chemistry, 1986, 11724-11729, vol. 380.

Varro et al., Ann Clin Biochem, 2003, 472-480, vol. 40.

Rahier et al., Biosynthesis of Gastrin, Gastronenterology, 1987, 1146-1152, vol. 92.

(Continued)

*Primary Examiner* — Gailene R Gabel
*Assistant Examiner* — Christine Foster
(74) *Attorney, Agent, or Firm* — Jenkins, Wilson, Taylor & Hunt, P.A.

(57) ABSTRACT

The invention provides assay methods for the detection and quantitation of gastrin hormones, including total and free gastrin hormone in a sample. ELISA-type heterogeneous phase assays suitable for use with biological fluid samples such as blood, plasma or other bodily fluids of a mammal, particularly a human subject are provided. The method provides a precise assay for the amounts of free and total G17 and G34 in biological fluid samples, as well as the amounts of free and total Gly-extended G17, and Gly-extended G34. Also provided are methods of determining suitable treatment for patient suffering from a gastrin hormone-mediated disease or condition employing gastrin hormone immunoassays.

9 Claims, 2 Drawing Sheets

U.S. PATENT DOCUMENTS

| | | | |
|---|---|---|---|
| 5,733,790 A * | 3/1998 | Potter et al. ................ | 436/518 |
| 5,736,146 A | 4/1998 | Cohen et al. | |
| 5,750,119 A | 5/1998 | Srivastava | |
| 5,759,551 A | 6/1998 | Ladd et al. | |
| 5,759,791 A | 6/1998 | Kuhajda et al. | |
| 5,767,242 A | 6/1998 | Zimmermann et al. | |
| 5,770,576 A | 6/1998 | Morozov et al. | |
| 5,785,970 A | 7/1998 | Gevas et al. ............... | 424/184.1 |
| 5,786,213 A | 7/1998 | Singh et al. | |
| 5,788,964 A | 8/1998 | Baral et al. | |
| 5,827,691 A | 10/1998 | Iwaki et al. | |
| 5,843,446 A | 12/1998 | Ladd et al. ................ | 424/184.1 |
| 5,866,128 A | 2/1999 | Gevas et al. ............... | 424/184.1 |
| 5,869,045 A | 2/1999 | Hellstrom et al. | |
| 5,869,058 A | 2/1999 | Cohen et al. | |
| 5,879,898 A | 3/1999 | Tarin et al. | |
| 5,932,412 A | 8/1999 | Dillner et al. .................... | 435/5 |
| 5,981,167 A | 11/1999 | Taremi et al. .................... | 435/4 |
| 6,132,720 A | 10/2000 | Grimes et al. | |
| 6,169,173 B1 | 1/2001 | Wank .......................... | 536/23.5 |
| 6,180,370 B1 | 1/2001 | Queen et al. | |
| 6,187,536 B1 | 2/2001 | Weinberg et al. | |
| 6,191,290 B1 | 2/2001 | Safavy | |
| 6,251,581 B1 | 6/2001 | Ullman et al. | |
| 6,303,123 B1 | 10/2001 | Grimes et al. ............ | 424/184.1 |
| 6,320,022 B1 | 11/2001 | Cutitta et al. | |
| 6,359,114 B1 | 3/2002 | Grimes et al. ............... | 530/344 |
| 6,391,299 B1 | 5/2002 | Blackburn et al. | |
| 6,548,066 B1 | 4/2003 | Michaeli et al. .......... | 424/185.1 |
| 6,565,813 B1 | 5/2003 | Garyantes .................... | 422/102 |
| 6,613,530 B1 | 9/2003 | Wienhues et al. | |
| 6,627,196 B1 | 9/2003 | Baughman et al. | |
| 6,639,055 B1 | 10/2003 | Carter et al. | |
| 6,689,869 B2 | 2/2004 | Waldmann et al. | |
| 6,696,262 B2 | 2/2004 | Härkönen | |
| 6,699,974 B2 | 3/2004 | Ono et al. | |
| 6,780,969 B2 | 8/2004 | Wang | |
| 6,815,414 B2 | 11/2004 | Chowers et al. | |
| 6,861,510 B1 | 3/2005 | Gevas et al. ............... | 530/388.1 |
| 7,074,761 B1 * | 7/2006 | Hinuma et al. ................ | 514/12 |
| 7,235,376 B2 | 6/2007 | Grimes et al. | |
| 7,300,918 B2 | 11/2007 | Rath | |
| 2001/0020005 A1 | 9/2001 | Chowers et al. | |
| 2002/0058040 A1 | 5/2002 | Grimes et al. ............ | 424/185.1 |
| 2002/0095028 A1 | 7/2002 | Grimes et al. ............ | 530/412 |
| 2003/0021786 A1 | 1/2003 | Gevas et al. ............... | 424/185.1 |
| 2003/0049698 A1 | 3/2003 | Wang | |
| 2003/0068326 A1 | 4/2003 | Gevas et al. ............... | 424/185.1 |
| 2003/0082643 A1 | 5/2003 | Hudson et al. | |
| 2003/0086941 A1 | 5/2003 | Michaeli et al. .......... | 424/185.1 |
| 2003/0091574 A1 | 5/2003 | Gevas et al. ............... | 424/155.1 |
| 2003/0138860 A1 | 7/2003 | Robertson et al. | |
| 2003/0232399 A1 | 12/2003 | Robertson et al. | |
| 2004/0001842 A1 | 1/2004 | Michaeli et al. .......... | 424/185.1 |
| 2004/0063164 A1 | 4/2004 | Lassalle | |
| 2004/0266682 A1 | 12/2004 | Cruz | |
| 2005/0025770 A1 | 2/2005 | Gevas et al. ............... | 424/155.1 |
| 2005/0069966 A1 | 3/2005 | Grimes et al. | |
| 2005/0169979 A1 | 8/2005 | Michaeli et al. .......... | 424/184.1 |
| 2005/0187152 A1 | 8/2005 | Gevas et al. ................ | 514/12 |
| 2006/0020119 A1 | 1/2006 | Grimes et al. ............ | 530/388.1 |
| 2006/0039911 A1 | 2/2006 | Gevas et al. ............... | 424/145.1 |
| 2006/0140962 A1 | 6/2006 | Gevas et al. ............... | 424/155.1 |
| 2007/0031511 A1 | 2/2007 | Baldwin et al. | |
| 2007/0065454 A1 | 3/2007 | Michaeli et al. | |
| 2007/0066809 A1 | 3/2007 | Grimes et al. | |
| 2007/0082043 A1 | 4/2007 | Michaeli et al. | |
| 2007/0248608 A1 | 10/2007 | Grimes et al. | |
| 2009/0004200 A1 | 1/2009 | Gevas et al. | |
| 2009/0191232 A1 | 7/2009 | Gevas et al. | |

FOREIGN PATENT DOCUMENTS

| | | |
|---|---|---|
| EP | 0 755 683 | 1/1997 |
| EP | 0818680 | 1/1998 |
| EP | 1 129 724 | 9/2001 |
| EP | 1579863 | 9/2005 |
| JP | 06107564 A | 4/1994 |
| WO | WO 90/08774 | 8/1990 |
| WO | WO94/00590 | 1/1994 |
| WO | WO95/04544 | 2/1995 |
| WO | WO 95/13297 | 5/1995 |
| WO | WO95/21380 | 8/1995 |
| WO | WO96/15456 | 5/1996 |
| WO | WO97/28821 | 8/1997 |
| WO | WO97/38584 | 10/1997 |
| WO | WO98/31393 | 7/1998 |
| WO | WO 98/51337 | 11/1998 |
| WO | WO99/19353 | 4/1999 |
| WO | WO 99/59612 | 11/1999 |
| WO | WO 99/59628 | 11/1999 |
| WO | WO 99/59631 | 11/1999 |
| WO | WO99/65513 | 12/1999 |
| WO | WO00/67035 | 11/2000 |
| WO | WO01/13114 | 2/2001 |
| WO | WO01/34192 | 5/2001 |
| WO | WO 01/77685 A2 | 10/2001 |
| WO | WO02/39123 | 5/2002 |
| WO | WO 02/076499 | 10/2002 |
| WO | WO03/005955 | 1/2003 |
| WO | WO 2004/023148 | 3/2004 |
| WO | WO2004/023148 | 3/2004 |
| WO | WO 2004/088326 | 10/2004 |
| WO | WO 2005/095459 | 10/2005 |
| WO | WO 2006/008649 | 1/2006 |
| WO | WO 2006/016275 | 2/2006 |
| WO | WO 2006/032980 | 3/2006 |

OTHER PUBLICATIONS

Kokthary et al., Regulatory Peptides, 1987, 71.84, vol. 17.
Ardill et al., QJ Med, 1998; 739-742, vol. 91.
Seva, et al., Science, 1994, 410-412, vol. 265.
Smith et al., The British Journal of Surgery, 1998, 1285-1289, vol. 85.
Todisco et al., The Journal of Biological Chemistry, 1995, 28337-28341, vol. 270.
Watson et al., Br. J. Cancer, 1989, 554-558, vol. 59.
Varro et al., The Journal of Biological Chemistry, 1994, 20764-20770, vol. 269.
Dickinson et al., The Journal of Biological Chemistry, 1991, 334-338, vol. 266.
Kelly et al., Journal of Gastroenterology and Hepatology, 1998, 208-214, vol. 13.
Rehfeld et al., Cancer Research, 1989, 2840-2843, vol. 49.
Smith et al., Gut, 2000, 820-824, vol. 47.
Watson et al., Cancer Research, 2001, 625-631, vol. 61.
Hughes et al., Digestive Diseases, 1976, 201-204, vol. 21.
Jaffe, et al., Surgery, 1969, 633-639, vol. 65.
Dockray, et al., The Gastrins: Their Production and Biological Activities, 119-139, (2001).
Smith et al., Alimentary Pharmacology & Therapeutics, 1231-1247, vol. 14, (2000).
Dickinson et al., Gastroenterology, 1995, 1384-1388, vol. 109.
Rehfeld et al., Biochimica et Biophysic Acta, 1972, 364-372, vol. 285.
Nemeth et al., Gut, 1993, 90-95, vol. 34.
Varndell, et al., Experienta, 1983, 713-717, vol. 39.
Watson, S. Exp. Opin. Invest. Drugs, 1995, 1253-1266, vol. 4.
Watson, et al., Gastrin Receptors in Gastrointestinal Tumors, 1993, 1-91, CRC Press, Boca Raton, FL.
Caplin, et al., Journal of Hepatology, 1999, 519-526, vol. 30.
Henwood, et al., British Journal of Surgery, 2001, 564-568, vol. 88.
Watson, et al., Int. J. Cancer, 1998, 873-877, vol. 75.
Watson, et al., Int. Cancer, 1999, 248-254, vol. 81.
Watson, et al., Cancer Research, 1996, 880-885, vol. 56.
Watson, et al., Cancer Research, 2001, 625-631, vol. 61.
Watson, et al., Reports, 1991, 866-871, vol. 83, J. Natl Cancer.
Watson, et al., Growth Enhancing effects of Gastrin, 1998, 554-558, Inst. Br. J. Cancer vol. 59.
Watson, et al., Exp. Opin. Invest. Drugs, 1995, 1253-1266, vol. 4.
Watson, et al., Human Progastrin Expression, 1996, 1918-1929, vol. 98.
Watson, et al., Exp. Opin. Ther., 2001, 309-317, vol. 1.
Hoff, et al., Current Opinion in Oncology, 2002, 621-627, vol. 14.

Gilliam, et al., EJSO, 2004, 536-543, vol. 30.
Kovacs, et al, Gastroenterology, 1989, 1406-1413, vol. 97.
Makishima, et al., Faseb Journal, 1994, A92, vol. 8 Abs 535.
Smith, et al., Clinical Cancer Research, 2000, 4719-4724, vol. 6.
His, MD, Arch Pathol Lab Med, 2001, 289-294, vol. 125.
Cole, Clinical Chemistry, 1997, 2233-2243, vol. 43.
Feurle, et al, Pancreas, 1995, 281-286, vol. 10.
Ohning, et al., Peptides, 1994, 417-587, vol. 15.
Kovacs, et al., Peptides, 1996, 583-587, vol. 17.
Ohning, et al., The American Journal Physiological Society, 1996, G470-476.
Sipponen, et al., Scand J Gastroenterol, 2002, 785-791, vol. 7.
Dockray, et al., Gastroenterology, 1975, 222-230, vol. 68.
Smith, et al., American Journal Physiology, 1996, R1078-R1084, vol. 270.
Smith, et al., American Journal Physiology, 1995, R135-R141, vol. 286.
Smith, et al., American Journal Physiology, 1994, R277-283, vol. 266.
Yanaihara, et al., Gut Peptides, 1979, 26-33.
Kovacs, et al., American Journal Physiology, 1997, G399-403, vol. 273 (2 Pt 1).
Vaananen et al., European J. Gastrolenterology, 2003, 885-891, vol. 15 (Pt 8).
Du et al., J Biotechnology, 2003, 87-100, vol. 106 (1).
Tetin et al., Current Pharm. BioTechnol. 2004, 9-16, vol. 5 (Pt 1).
Onorato et al., NY Acad. Sci. 1998, 277-290, vol. 1998.
Plested et al., Methods Mol. Med. 2003, 243-261, vol. 71.
Rondeel, et al., Expert Rev. Mol. Diagnos. 2002, 226-232, vol. 2 (Pt 3).
Bailey et al., Methods Mol. Biol. 1994, 449-459, vol. 32.
Kovacs, T.O. et al., (Aug. 1997) "Inhibition of sham feeding-stimulated . . . " Am J Physiol. 273 (2 Pt 1): G399-403.
Vaananen H., et al. (Aug. 2003) "Non-endoscopic diagnosis of atrophic gastritis . . . " Eur J. Gastroenterol. 15(8) 885-891.
Du W., Xu Z., Ma X., Song L., and Schneider (Dec. 2003) Biochip as a potential platform . . . ) J Blotechnol. (Dec. 2003) 106 (1): 87-100.
Tetin S., Y., et al. (Feb. 2004) Antibodies in diagnostic applications Curr Pharm Biotechnol 5 (1): 9-16.
Onorato J.M., et al. (Nov. 1998) "Immunohistochemical and ELISA assays . . . " NY Aced Sci 854: 277-290.
Plested J.S. et al. (2003) Methods Mol Med 71: 243-261.
Rondeel J.M., (May 2002) "Immunofluorescence versus ELISA . . . " Expert Rev Mol Diagn. 2(3): 266-232.
Bailey G.S., (1994) "Radioimmunoassay of Peptides and Protein" Methods Mol Biol. 32: 449-459.
Sugano et al., The Journal of Biological Chemistry, 1986, 11724-11729, vol. 380.
Rahier et al., Biosynthesis of Gastrin, Gastronenterology, 1987, 1146-1152, vol. 92.
Kokthary et al., Regulatory Peptides, 1987, 71-84, vol. 17.
Todisco et al., The Journal of Biological Chemistry, 1995, 28337-28341, vol. 270.
Varro et al., The Journal of Biological Chemistry, 1994, 20764-20770, vol. 269.
Dickinson et al., The Journal of Biological Chemistry, 1991, 334-338, vol. 266.
Kelly et al., Journal of Gastroenterology and Hepatology, 1998, 208-214, vol. 13.
Dockray, et al., The Gastrins: Their Production and Biological Activities, 119-139, 2001.
Smith et al., Alimentary Pharmacology & Therapeutics, 1231-1247, vol. 14, 2000.
Wang, et al., Human Progastrin, J. Clin Invest. 1996, 1918-1929, vol. 98.
Hsi, MD, Arch Pathol Lab Med, 2001, 289.294, vol. 125.
Feurle, et al., Pancreas, 1995, 281-286, vol. 10.
Ohning, et al., Peptides, 1994, 417-423, vol. 15.
Ohning, et al., The American Journal Physiological Society, 1996, G470-476.
Abrahm et al., "Development and evaluation of a high affinity species and region specific monoclonal antibody to human gastrin," Gastroenterology, 86(5(2)):1012, (1984).

Aphton Biophanna BIO2005 Presentation, Jun. 19-22, Philadelphia, PA (2005), 26 pages.
Ausubel, ed., "Current Protocols in Molecular Biology," John Wiley & Sons, New York, pp. 11.15.1-11.15.4. (1990).
Blackmore et al. "Autocrine growth stimulation of human renal Wilms' tumour G401 cells by a gastrin-like peptide," International Journal of Cancer, 57:385-3912 (1994).
Caplin et al., "Serum gastrin levels and identification of CCK-B-gastrin receptor following partial hepatectomy for liver tumours in man," Gastroenterology, 110(4 suppl.) A1162, (1996).
Caplin et al., "Demonstration of new sites of expression of the CCK-B/gastrin receptor in pancreatic acinar AR42J cells using immunoelectron microscopy," Regulatory Peptides, 84(1-3):81-89, (1999).
Caplin et al., "Effect of gastrin and anti-gastrin antibodies on proliferation of hepatocyte cell lines," Digestive Diseases and Sciences, 46(7):1356-1366, (2001).
Ciccotosto et al., "Expression, processing, and secretion of gastrin in patients with colorectal carcinoma," Gastroenterology, 109(4):1142-1153, (1995).
"Gastrin 17 vaccine—Aphton: Anti-gastrin 17 immunogen, G17DT," Biodrugs 17(3):223-225 (2003).
Gocyk et al., "Helicobacter pylori, gastrin and cyclooxygenase-2 in lung cancer," Med. Sci. Monit. 6(6):1085-1092 (2000).
Halter et al., "Evaluation of a monoclonal anti-gastrin antibody as a tool for immunoneutralization of gastrin during omeprazole treatment in the rat", *Gastroenterology* (96(5) part 2:A194 (1989).
Harris et al., "An antiapoptotic role for gastrin and the gastrin/CCK-2 receptor in Barrett's esophagus," Cancer Res. 64(6):1915-1919 (2004).
Helander et al., "Immunohistochemical localization of gastrin/CCK-B receptors in the dog and guinea-pig stomach," Acta Physiologica Scandinavica, 159:(4)313-320, (1997).
Herget et al., "Cholecystokinin stimulates Ca2+ mobilization and clonal growth in small cell lung cancer through CCKA and CCKB/gastrin receptors," Annals of the New York Academy of Sciences, 713:283-297, (1994).
Janeway et al. "Immunobiology: the immune system in health and disease", Fourth Edition, 1999, Elsevier Science Ltd, Garland Publishing, p. 544.
Joshi et al., "Gastrin and Colon Cancer: a unifying hypothesis" *Digestive Diseases* 14:334-344 (1996).
Kohler et al., "Continuous cultures of fused cells secreting antibody of predefined specificity", Nature 256:495-497 (1975).
McWilliams et al., "Antibodies raised against the extracellular tail of the CCKB/gastrin receptor inhibit gastrin-stimulated signaling," Regulatory Peptides, 99(2-3):157-161, (2001).
Mishell et al., "Selected Methods in Cellular Immunology" (Chapter 17: Immunoglobulin Producing Hybrid Cell Lines), Freeman and Co., San Francisco, 1980).
Mulholland et al., "Elevated Gastric Acid Secretion in Patients with Barrett's Metaplastic Epithelium" Digestive Diseases and Sciences, 34(9):1329-1334, (1989).
Smith et al., "Characterization of the CCK-C (cancer) receptor in human pancreatic cancer" *Int. J. Mol. Medicine* 10(6):689-694 (2002).
Smith et al., "Gastrin may have an autocrine/paracrine role in Barrett's oesophagus and oesophageal adenocarcinoma," British Journal of Surgery, 84:706-707, (1997).
Tarasova et al. "Anti-peptide antibodies specific for the gastrin-cholecystokinin-B receptor," Letters in Peptide Science, 1:221-228, (1995).
Tarasova et al., "Endocytosis of gastrin in cancer cells expressing gastrin/CCK-B receptor" *Cell and Tissue Research*, 287:325-333 (1997).
Thorndyke, "Identification and localization of material with gastrin-like immunoreactivity in the neutral ganglion of a photochordate, Ciona intestinalis." *Regulatory Peptides* 16:269-279 (1986).
Watson et al., "Antibodies targeting the amino terminal portion of the human CCKB/gastrin receptor inhibit the liver invasion of a human colonic tumor," Gastroenterology 114(4 Part 2): A701 (Abstract # G2899) (Apr. 15, 1998).

Watson et al., "Effect of gastrin neutralization on the progression of the adenoma:carcinoma sequence in the Min mouse model of familial adenomatous polyposis," Gastroenterology 114(Supplement 1): A701 (Abstract #G2900) (Apr. 15, 1998).

Watson et al., "Growth-promoting action of gastrin on human colonic and gastric tumour cells cultured in vitro" Br. J. Surg. 75(4):342-345 (1988).

Watson et al., "Inhibitory effects of the gastrin receptor antagonist (L-365,260) on gastrointestinal tumor cells," Cancer, 68:1255-1260, (1991).

Watson et al., "Anti-gastrin antibodies raised by gastrimmune inhibit growth of colorectaltumor AP5" Int. J. Cancer, 61(2):233-240 (1995).

Watson et al., "Expression of gastrin-CCKB receptor isoforms in gastrointestinal tumor cells: Relationship to gastrin secretion," Proceedings of the American Association for Cancer Research Annual Meeting, 38(0):116 (Abstract 773), (1997).

Watson et al., "Antiserum raised against an epitope of the cholecystokinin B/gastrin receptor inhibits hepatic invasion of a human colon tumor," Cancer Research, 60(20):5902-5907, (2000).

Watson et al., "Antibodies raised by gastrimmune inhibit the spontaneous metastasis of a human colorectal tumour AP5LV," European Journal of Cancer, 35(8):1286-1291, (1999).

Watson et al., "Antibodies targeting the Amino Terminal portion of the Human CCKB/gastrin receptor inhibit the liver invasion of a human colonic tumour," Research Presentation, Digestive Disease Week, American Gastroenterological Association (1998), 17 slides.

Watson et al., "Inhibition of gastrin-stimulated growth of gastrointestinal tumour cells by octreatide and the gastrin/ cholecystokinin receptor antagonists, proglumide and lorglumide," European Journal of Cancer, 28A(8-9):1462-1467, (1992).

Watson et al., "The in vitro growth response of primary human colorectal and gastric cancer cells to gastrin," International Journal of Cancer, 43:692-696, (1989).

Watson et al., "Therapeutic effect of the gastrin receptor antagonist, CR2093 on gastrointestinal tumour cell growth," British Journal of Cancer, 65(6):879-883, (1992).

Azuma et al., Immunocytochemical evidence for differential distribution of gastrin forms using region-specific monoclonal antibodies. Gastroenterology. vol. 21, No. 4 pp. 319-324 (1986).

Berg et al., Biochemistry. New York: W.H. Freeman and Co.: 2002, Sections 4.3.1-4.3.3 and Figure 4.35.

Goetze et al., Impact of Assay Epitope Specificity in Gastrinoma Diagnosis. Clinical Chemistry. vol. 49 pp. 333-334 (2003).

Notice of Allowance corresponding to U.S. Appl. No. 10/813,336 dated May 15, 2006.

Notice of Allowance corresponding to U.S. Appl. No. 10/813,336 dated Oct. 3, 2006.

Notice of Allowance corresponding to U.S. Appl. No. 10/813,336 dated Feb. 7, 2007.

Official Action corresponding to Canadian Patent Application No. 2,520,010 dated Aug. 17, 2009.

Official Action corresponding to Canadian Patent Application No. 2,561,405 dated Jul. 31, 2009.

Official Action corresponding to Chinese Patent Application No. 200580017341.9 dated Jun. 19, 2009.

Official Action corresponding to U.S. Appl. No. 10/813,336 dated Jun. 23, 2005.

Official Action corresponding to U.S. Appl. No. 10/813,336 dated Oct. 20, 2005.

Official Action corresponding to U.S. Appl. No. 11/093,724 dated Nov. 25, 2005.

Official Action corresponding to U.S. Appl. No. 11/093,724 dated Feb. 6, 2006.

Official Action corresponding to U.S. Appl. No. 11/499,261 dated Mar. 15, 2007.

Official Action corresponding to U.S. Appl. No. 11/499,261 dated Nov. 30, 2007.

Official Action corresponding to U.S. Appl. No. 11/499,261 dated Sep. 24, 2008.

Official Action corresponding to U.S. Appl. No. 11/499,261 dated May 14, 2009.

Rehfeld et al., Residue-specific immunochemical sequence prediction. Journal of Immunological Methods. vol. 171 pp. 139-142 (1994).

Notice of Acceptance corresponding to Australian Patent Application No. 2005228897 dated Nov. 25, 2009.

Notification of Transmittal of the International Search Report and the Written Opinion of the International Searching Authority, or the Declaration corresponding to International Application No. PCT/US2004/009666 dated Nov. 8, 2004.

Notification of Transmittal of the International Search Report and the Written Opinion of the International Searching Authority, or the Declaration corresponding to International Application No. PCT/US2005/010532 dated Feb. 8, 2006.

Official Action corresponding to Australian Patent Application No. 2004225437 dated Dec. 15, 2009.

Official Action corresponding to Japanese Patent Application No. 2006-509465 dated Oct. 21, 2009.

Akai, "Co-existence and co-release of Gastrin 34 N-terminal Fragment with Gastrin 17 in Rat Stomach," Folia endocrinol, 64:1065-1080 (1988) [ABSTRACT].

Abdalla et al., "Gastrin-Induced Cyclooxygenase-2 Expression in Barrett's Carcinogenesis," Clinical Cancer Research. vol. 10 pp. 4784-4792 (2004).

Ajani et al., "Phase I and II Studies of the Combination of Recombinant Human Interferon-γ and 5-Fluorouracil in Patients with Advanced Colorectal Carcinoma," Journal of Biological Response Modifiers. vol. 8, No. 2 pp. 140-146 (1989).

Ardis R&D Profile, "Gastrin 17 vaccine—Aphton: Anti-gastrin 17 immunogen, G17DT," Biodrugs. vol. 17, No. 3 pp. 223-225 (2003).

Asao et al., "Eradication of Hepatic Metastases of Carcinome H-59 by Combination Chemimmunotherapy with Liposomal Muramyl Tripeptide, 5-Fluorouracil, and Leucovorin," Cancer Research. vol. 52 pp. 6254-6257 (1992).

Baldwin et al., "Binding of the progastrin fragments to the 78 kDa gastrin-binding protein," FEBS Lett. vol. 359 pp. 97-100 (1995).

Baldwin, G.S. and Shulkes, A., "Gastrin, gastrin receptors and colorectal carcinoma," Gut. vol. 42 pp. 581-584 (1998).

Baldwin, G.S., and Zhang, Q., "Measurement of Gastrin and Transforming Growth Factor α Messenger RNA Levels in Colonic Carcinoma Cell Lines by Quantitative Polymerase Chain Reaction," Cancer Research. vol. 52 pp. 2261-2267(1992).

Ballantyne, G.H., and Quin, J., "Surgical Treatment of Liver Metastasis in Patients with Colorectal Cancer," Cancer. vol. 71, No. 12 pp. 4252-4266 (1993).

Beacham et al., "Human Gastrin: Isolation, Structure and Synthesis: Synthesis of Human Gastrin I," Nature. vol. 209, No. 5023 pp. 585-586 (1966).

Beauchamp et al., "Proglumide, A Gastrin Receptor Antagonist, Inhibits Growth of Colon Cancer and Enhances Survival in Mice," Ann. Surg. vol. 202, No. 3 pp. 303-308 (1985).

Behr et al., "Cholecystokinin-B/Gastrin Receptor Binding Peptides: Preclinical Development and Evaluation of Their Diagnostic and Therapeutic Potential," Clinical Cancer Research. vol. 5 pp. 3124s-3138s (1999).

Beinborn et al., "A single amino acid of the cholecystokinin-B/gastrin receptor determines specificity for non-peptide antagonists," Nature. vol. 362 pp. 348-350 (1993).

Biagini et al., "The Human Gastrin/Cholecystokinin Receptors: Type B and Type C Expression in Colonic Tumours and Cell Lines," Life Sciences. vol. 61, No. 10 pp. 1009-1018 (1997).

Bodey, "The significance of immunohistochemistry in the diagnosis and therapy of neoplasms," Expert Opin. Biol. Ther. vol. 2, No. 4 pp. 371-393 (2002).

Boland, "Editiorial: Gastrin and Colorectal Neoplasia—Chicken or Egg, or Both?" J. Clin. Gastroenterology. vol. 13, No. 5 pp. 497-499 (1991).

Boon, "Toward a Genetic Analysis of Tumor Rejection Antigens," Advances in Cancer Research. vol. 58 pp. 177-210 (1992).

Bowie et al., "Deciphering the Message in Protein Sequences: Tolerance to Amino Acid Substitutions," Science. vol. 247 pp. 1306-1310 (1990).

Buchan et al., "Regulatory Peptides in Barrett's Esophagus," Journal of Pathology. vol. 146, No. 3 pp. 227-234 (1985).

Burris III et al., "Improvements in survival and clinical benefit with gemcitabine as first-line therapy for patients with advanced pancreas cancer: a randomized trial," Journal of Clinical Oncology. vol. 15, No. 6 pp. 2403-2413 (1997).

Bystryn, J., "Tumor vaccines," Cancer and Metastasis Reviews. vol. 9 pp. 81-91 (1990).

Caplin et al., "Expression and processing of gastrin in pancreatic adenocarcinoma," Brit. J. Surgery. vol. 87 pp. 1035-1040 (2000).

Caplin et al., "Expression and Processing of Gastrin in Patients with Hepatocellular Carcinoma, Fibrolamellar Carcinoma and Cholangiocarcinoma," Gastroenterology. vol. 114, Suppl. I p. A1219 (1998) [ABSTRACT # L0083].

Casper et al., "Phase II trial of gemcitabine (2,2'-difluorodeoxycitidine) in patients with adenocarcinoma of the pancreas," Investigational New Drugs. vol. 12, No. 1 pp. 29-34 (1994) [ABSTRACT].

Chaudhry et al., "Phase I and Imaging Trial of a Monoclonal Antibody Directed Against Gastrin-releasing Peptide in Patients with Lung Cancer," Clinical Cancer Researc. vol. 5 pp. 3385-3393 (1999).

Choudhury et al., "$N$-Terminal Sequence of Human Big Gastrin: Sequence, Synthetic and Immunochemical Studies," A76 Hoppe-Seyler's Z. Physiol. Chem. vol. 361 pp. 1719-1733 (1980).

Clerc et al., "Differential Expression of the CCK-A and CCK-B/Gastrin Receptor Genes in Human Cancers of the Esophagus, Stomach, and Colon," International Journal of Cancer. vol. 72 pp. 931-936 (1997).

de Jong et al., "Effects of partial liver resection on tumor growth," Journal of Hepatology. vol. 25 pp. 109-121 (1996).

De Magistris, L., and Rehfeld, J.F., "A Simple Enzymatic Procedure for Radioimmunochemical Quantitation of the Large Molecular Forms of Gastrin and Cholecystokinin," Analytical Biochemistry. vol. 102 pp. 126-133 (1980).

Deed of Letters Patent corresponding to Australian Patent Application No. 2004225437 dated Aug. 26, 2010.

Del Valle et al., "Progastrin and Its Glycine-Extended Post-translational Processing Intermediates in Human Gastrointestinal Tissues," Gastroenterology. vol. 92, No. 6 pp. 1908-1912 (1987).

Dethloff et al., "Inhibition of Gastrin-Stimulated Cell Proliferation by the CCK-B/gastrin Receptor Ligand CI-988," Food and Chemical Toxicology. vol. 37 pp. 105-110 (1999).

Dockray et al., "Gastric Endocrine Cells: Gene Expression, Processing, and Targeting of Active Products," Physiological Review. vol. 76, No. 3 pp. 767-798 (1996).

Dockray et al., "Immunochemical studies on big gastrin using $NH_2$-terminal specific antiserums," Regulatory Peptides. vol. 1, No. 3 pp. 169-186 (1980). Chemical Abstracts vol. 94 pp. 506-507 (1981) [ABSTRACT #94:119200w].

Dockray, "Immunochemical Studies on Big Gastrin Using $NH^2$-Terminal Specific Antisera," Regulatory Peptides. vol. 1 pp. 169-186 (1980).

Dockray, G.J., and Taylor, I.L., "Heptadecapeptide Gastrin: Measurement in Blood by Specific Radioimmunoassay", Gastroenterology. vol. 71, No. 6 pp. 971-977 (1976).

Douziech et al. "Growth Effects of Regulatory Peptides and Intracellular Signaling Routes in Human Pancreatic Cancer Cell Lines," Endocrine. vol. 9, No. 2 pp. 171-183 (1998).

Edkins, J.S., "On the Chemical Mechanism of Gastric Secretion," Proceedings of the Royal Society of London. Series B, Containing Papers of a Biological Character. vol. 76, No. 510 p. 376 (1905).

Edkins, J.S., "The Chemical Mechanism of Gastric Secretion," J. Physiol. vol. 34, Nos. 1-2 pp. 133-144 (1906).

Erlichman et al., "A Randomized Trial of Fluorouracil and Colonic Acid in Patients With Metastatic Colorectal Carcinoma," Journal of Clinical Oncology. vol. 6 pp. 469-475 (1988).

Ezzell, C., "Cancer 'Vaccines': An Idea Whose Time Has Come?" The Journal of NIH Research. vol. 7 pp. 46-49 (1995).

Finley et al., "Expression of the Gastrin Gene in the Normal Human Colon and Colorectal Adenocarcinoma," Cancer Research. vol. 53 pp. 2919-2926 (1993).

Fourmy et al., "Relationship of CCK/gastrin-receptor binding to amylase release in dog pancreatic acini," Regulatory Peptides. vol. 10 pp. 57-68 (1984).

Frucht et al., "Characterization of Functional Receptors for Gastrointestinal Hormones on Human Colon Cancer Cells," Cancer Research. vol. 52, No. 5 pp. 1114-1122 (1992).

Gilliam et al., "Randomized, double blind, placebo-controlled, multi-centre, group-sequential trial of G17DT for patients with advanced pancreatic cancer unsuitable or unwilling to take chemotherapy," Journal of Clinical Oncology. ASCO Annual Meeting Proceedings. vol. 22, No. 14S p. 2511 (2004) [ABSTRACT].

Goletti et al. "Resection of Liver Gastrinoma Leading to Persistent Eugastrinemia," Eur. J. Surgery. vol. 158 pp. 55-57 (1992).

Gregory, R.A., and Tracy, H.J., "Isolation of Two Gastrins from Human Antral Mucosa," Nature. vol. 209, No. 5023 p. 583 (1966).

Grider, J.R., and Makhlouf, G.M., "Distinct receptors for cholecystokinin and gastrin on muscle cells of stomach and gallbladder," Am. J. Physiol. vol. 259 pp. G184-G190 (1990).

Gupta, J.R., and Siber, G.R., "Adjuvants for human vaccines—current status, problems and future prospects," Vaccine. vol. 13, No. 14 pp. 1263-1276 (1995).

Gura, T., "Systems for Identifying New Drugs Are Often Faulty," Science. vol. 278, No. 5340 pp. 1041-1042 (1997).

Haigh et al. "Gastrin Induces Proliferation in Barrett's Metaplasia Through Activation of the $CCK_2$ Receptor," Gastroenterology. vol. 124 pp. 615-625 (2003).

Hananel et al., "Hepatic Resection for Colorectal Liver Metastasis," The American Surgeon. vol. 61, No. 5 pp. 444-447 (1995).

Harlow and Lane, Antibodies: A Laboratory Manual, Cold Spring Harbor Laboratory Press. pp. 7-13, 23-26, 142-143, 148-149 (1988).

Hellmich et al., "Human Colorectal Cancers Express a Constitutively Active Cholecystokinin-B/Gastrin Receptor That Stimulates Cell Growth," The Journal of Biological Chemistry. vol. 275, No. 41 pp. 32122-32128 (2000).

Herbert et al. (Eds.) "The Dictionary of Immunology," $3^{rd}$ Ed. Academic Press, London, p. 41 (1995).

Hoosein et al., "Antiproliferative Effects of Gastrin Receptor Antagonists and Antibodies to Gastrin on Human Colon Carcinoma Cell Lines," Cancer Research. vol. 48 pp. 7179-7183 (1988).

Hoosein et al., "Evidence for Autocrine Growth Stimulation of Cultured Colon Tumor Cells by a Gastrin/Cholecystokinin-like Peptide," Experimental Cell Research. vol. 186, No. 1 pp. 15-21 (1990).

Houghten et al., "Relative Importance of Position and Individual Amino Acid Residues in Peptide Antigen-Antibody Interactions: Implications in the Mechanism of Antigenic Drift and Antigenic Shift," Vaccines. vol. 86 pp. 21-25 (1986).

Hughes et al., "Development of a class of selective cholecystokinin type B receptor antagonists having potent anxiolytic activity," PNAS. vol. 87 pp. 6728-6732 (1990).

Ichikawa et al., "Distinct effects of tetragastrin, histamine, and CCh on rat gastric mucin synthesis and contribution of NO," Am. J. Physiol. vol. 274, No. 1 pp. G138-G146 (1998).

Iwanaga et al., "Immunocytochemical Localization of the Different Gastrin Forms in the Pyloric Antrum," Biomedical Research. vol. 1 pp. 316-320 (1980).

Iwase et al., "Regulation of Growth of Human Gastric Cancer by Gastrin and Glycine-Extended Progastrin," Gastroenterology. vol. 113 pp. 782-790 (1997).

Jaffe et al., "Gastrin resistance following immunization to the C-terminal tetrapeptide amide of gastrin," Surgery. vol. 69, No. 2 pp. 232-237 (1971).

Jaffe et al., "Inhibition of Endogenous Gastrin Activity by Antibodies to the Carboxyl-Terminal Tetrapeptide Amide of Gastrin," Gastroenterology. vol. 58, No. 2 pp. 151-156 (1970).

Jain, R.K., "Barriers to Drug Delivery in Solid Tumors," Scientific American. vol. 171, No. 1 pp. 58-65 (1994).

Johnson et al, "Ornithine Decarboxylase in Large Bowel Mucosa: Regulation by Gastrin, Secretin and EGF," Journal of Physiology and Pharmacology. vol. 43, No. 1 pp. 33-41 (1992).

Johnson, "New Aspects of the Trophic Action of Gastrointestinal Hormones," Gastroenterology. vol. 72, No. 4, Part 2 pp. 788-792 (1977).

Kaiser, "First Pass at Cancer Genome Reveals Complex Landscape," Science. vol. 313 p. 1370 (2006).

Kameyama et al., "Adjuvant Chemo-Endocrine Chemotherapy with Gastrin Antagonist After Resection of Liver Metastasis in Colorectal Cancer," Japanese Journal of Cancer and Chemotherapy. vol. 21, No. 13 pp. 2169-2171 (1994) [ABSTRACT].

Katoh et al., "Malignant Zollinger-Ellison Syndrome. Stabilizing of Liver Metastasis After Gastrectomy with Resection of Primary Tumor," The American Surgeon. vol. 56, No. 6 pp. 360-363 (1990).

Kaufmann et al., "Cholecystokinin B-type receptor signaling is involved in human pancreatic cancer cell growth," Neuropeptides. vol. 31, No. 6 pp. 573-583 (1997).

Kelley et al., "Antitumor Activity of a Monoclonal Antibody Directed Against Gastrin-Releasing Peptide in Patients with Small Cell Lung Cancer," Chest. vol. 112 pp. 256-261 (1997).

Kobori et al., "Growth Responses of Rat Stomach Cancer Cells to Gastro-Entero-Pancreatic Hormones," International Journal of Cancer. vol. 30, No. 1 pp. 65-67 (1982).

Kochman et al, "Post-Translational Processing of Gastrin in Neoplastic Human Colonic Tissues," Biochemical and Biophysical Research Communications. vol. 189, No. 2 pp. 1165-1169 (1992).

Koh et al., "Gastrin Deficiency Results in Altered Gastric Differentiation and Decreased Colonic Proliferation in Mice," Gastroenterology. vol. 113, No. 3 pp. 1015-1025 (1997).

Koh et al., "Glycine-Extended Gastrin Promotes the Growth of Lung Cancer," Cancer Research. vol. 64 pp. 196-201 (2004).

Kopin et al. "Expression, cloning and characterization of the canine parietal cell gastrin receptor," PNAS. vol. 89 pp. 3605-3609 (1992).

Kusyk et al., "Stimulation of growth of a colon cancer cell line by gastrin," Am. J. Physiol. vol. 251 pp. G597-G601 (1986).

Lamberts et al., "Effects of Very Long (up to 10 years) Proton Pump Blockade on Human Gastric Mucosa," Digestion. vol. 64 pp. 205-213 (2001).

Lamers, C.B.H.W., and Jansen, J.B.M.J., "Role of Gastrin and Cholecystokinin in Tumours of the Gastrointestinal Tract," Eur. J. Cancer Clin. Oncol. vol. 24, No. 2 pp. 267-273 (1988).

Lamote, J., and Willems, G., "Stimulating effect of pentagastrin on cancer cell proliferation kinetics in chemically induced colon cancer in rats," Regulatory Peptides. vol. 20 pp. 1-9 (1988).

Larsson, L., and Rehfeld, J.F., "Characterization of Antral Gastrin Cells With Region-Specific Antisera," The Journal of Histochemistry and Cytochemistry. vol. 25, No. 12 pp. 1317-1321 (1977).

Larsson, "Histochemistry of Gastrin Cells," Neurohistochemistry: Modern Methods and Applications. Alan R. Liss, Inc., pp. 527-567 (1986).

Lee et al., "The Human Brain Cholecystokinin-B/Gastrin Receptor," The Journal of Biological Chemistry. vol. 268, No. 11 pp. 8164-8169 (1993).

Mahood et al., "Inhibition of Fluorouracil Stomatitis by Oral Cryotherapy," Journal of Clinical Oncology. vol. 9 pp. 449-452 (1991).

Makishima et al., "Active Immunization Against Gastrin-17 With an N-Terminal Derived Immunogen Inhibits Gastric and Duodenal Lesions in Rats," Gastroenterology. vol. 106, No. 4, Part. 2 p. A824 (1994) [ABSTRACT].

Mandair et al., "Cholecystokinin Receptors in Human Pancreatic Cancer Cell Lines," European Journal of Cancer. vol. 34, No. 9 pp. 1455-1459 (1998).

Marino et al., "Expression and Post-translational Processing of Gastrin in Heterologous Endocrine Cells," The Journal of Biological Chemistry. vol. 266, No. 10 pp. 6133-6136 (1991).

Martin et al. "Selection of Trypsin of 2 Sublines of Rat Cancer Cells Forming Progressive or Regressive Tumors," Int. J. Cancer. vol. 32 pp. 623-627 (1983).

Matsumoto et al. "Gastrin receptor characterization: affinity cross-linking of the gastrin receptor on canine gastric parietal cells," Am J. Physiol. vol. 252 p. G143-G147 (1987).

McGregor et al., "Trophic Effects of Gastrin on Colorectal Neoplasms in the Rat," Ann. Surg. vol. 195, No. 2 pp. 219-223 (1982).

McWilliams et al., "Coexpression of gastrin and gastrin-receptors (CCK-B and ΔCCK-B) in gastrointestinal tumour cell lines," Gut. vol. 42 pp. 795-798 (1998).

Miyake, "A Truncated Isoform of Human CCK-B/Gastrin Receptor Generated by Alternative Usage of a Novel Exon," Biochemical and Biohysical Research Communications. vol. 208, No. 1 pp. 230-237 (1995).

Mizutani et al., "Promotion of hepatic metastases by liver resection in the rat," British J. Cancer. vol. 65, No. 6 pp. 794-797 (1992).

Moertel, C.G., "Chemotherapy for Colorectal Cancer," The New England Journal of Medicine. vol. 330, No. 16 pp. 1136-1142 (1994).

Moody et al., "GRP Receptors Are Present in Non Small Cell Lung Cancer Cells," Journal of Cellular Biochemistry Supplement. vol. 24 pp. 247-256 (1996).

Moroder, L., and Wunsch, E., "Gastrins and Cholecystokinins: Chemical and Immunological Aspects," Gastrin and Cholecystokinin. Chemistry, physiology and pharmacology. (Ed. J. Bali et al.) Elsevier Science Publishers B.V. pp. 21-32 (1987).

MSNBC News Services, "Mixed results on new cancer drug," Nov. 9, 2000 (4 pages).

Mu et al., "Monoclonal antibody to the gastrin receptor on parietal cells recognizes a 78-kDa protein," PNAS. vol. 84 pp. 2698-2702 (1987).

Nakata et al., "Cloning and Characterization of Gastrin Receptor From ECL Carcinoid Tumor of Mastomys Natalensis," Biochemical and Biophysical Research Communications. vol. 187, No. 2 pp. 1151-1157 (1992).

Narayan et al., "Characterization of gastrin binding to colonic mucosal membranes of guinea pigs," Molecular and Cellular Biochemistry. vol. 112 pp. 163-171 (1992).

NCBI Accession No. NP 795344, retrieved from http://www.ncbi.nlm.nih.gov on Dec. 12, 2007 (4 pages).

Negre et al., "Autocrine Stimulation of AR4-2J Rat Pancreatic Tumor Cell Growth by Glycine-Extended Gastrin," Int. J. Cancer. vol. 66, No. 5 pp. 653-658 (1996).

Nemeth et al., "Development of a sequence-specific radioimmunoassay by using N-terminal gastrin 1-13 antibody," Chemical Abstracts. vol. 98 p. 495 (1983) [ABSTRACT # 98:51653], Abstract only.

Nieschlag, "Immunization With Hormones in Reproduction Research," North Holland Publishing Co., Amsterdam, Oxford. pp. 107-117 (1975).

Ochiai et,al., "Growth-Promoting Effect of Gastrin on Human Gastric Carcinoma Cell Line TMK-1," Japan Journal of Cancer Research. vol. 76 pp. 1064-1071 (1985).

Official Action corresponding to Canadian Patent Application No. 2,580,965 dated Sep. 30, 2010.

Official Action corresponding to Japanese Patent Application No. 2006-509465 dated Aug. 26, 2010.

Official Action corresponding to U.S. Appl. No. 11/499,621 dated Nov. 15, 2010.

Ohkura et al., "Gastrin-Enhanced Tumor Growth of a Xenotransplantable Human Gastric Carcinoma in Nude Mice," Jpn. J. Clin. Oncol. vol. 10, No. 2 pp. 255-263 (1980).

Okada et al., "Evaluation of cholecystokinin, gastrin, CCK-A receptor, and CCK-B/gastrin receptor gene expressions in gastric cancer," Cancer Letters. vol. 106, No. 2 pp. 257-262 (1996).

Osband, M.E., and Ross, S., "Problems in the investigational study and clinical use of cancer immunotherapy," Immunology Today. vol. 1, No. 6 pp. 193-195 (1990).

Pannequin et al., "Divergent roles for ferric ions in the biological activity of amidated and non-amidated gastrins," Journal of Endocrinology. vol. 181, No. 2 pp. 315-325 (2004).

Parsonnet et al., "*Helicobacter pylori* Infection and the Risk of Gastric Carcinoma," The New England Journal of Medicine. vol. 325, No. 16 pp. 1127-1131 (1991).

Pawlikowski et al., "Gastrin and Somatostatin Levels in Patients with Gastric Cancer," Horm. Metabol. Res. vol. 21 pp. 89-91 (1989).

Petrelli et al., "The Modulation of Fluorouracil With Leucovorin in Metastatic Colorectal Carcinoma: A Prospective Randomized Phase III Trial," Journal of Clinical Oncology. vol. 7 pp. 1419-1426 (1989).

Petrioli et al., "Treatment of Advanced Colorectal Cancer with High-dose Intensity Folinic Acid and 5-Fluorouracil Plus Supportive Care," European Journal of Cancer. vol. 31A, No. 12 pp. 2105-2108 (1995).

Power et al., "A novel gastrin-processing pathway in mammalian antrum," Chemical Abstracts. vol. 109, No. 9 p. 113 (1988) [ABSTRACT # 109:67341z].

Rae-Venter et al., "Gastrin Receptors in Human Colon Carcinoma," Gastroenterology. vol. 80, No. 5, Part 2 p. 1256 (1981) [ABSTRACT].

Redmond, E.J., and Wetscher, G.J., "Gastroesophageal Reflux Disease," Ronald Hinder ed., R.G. Landes Company. pp. 1-6 (1993).

Rehfeld et al., "Cell-specific processing of pro-cholecystokinin and pro-gastrin," Biochimie. vol. 70 pp. 25-31 (1988).

Rehfeld et al., "Production and Evaluation of Antibodies for the Radioimmunoassay of Gastrin," Scnad. J. Clin. Lab. Invest. vol. 30 pp. 221-232 (1972).

Rehfeld et al., "Sulfation of Gastrin: Effect on Immunoreactivity," Regulatory Peptides. vol. 2 pp. 333-342 (1981).

Rehfeld, J.F., "Gastrin and Colorectal Cancer: A Never-Ending Dispute?" Gastroenterology. vol. 108, No. 4 pp. 1307-1310 (1995).

Robertson et al., "Effect of Gastrointestinal Hormones and Synthetic Analogues on the Growth of Pancreatic Cancer," Int. J. Cancer. vol. 63 pp. 69-75 (1995).

Rodriguez-Lescure et al., "Phase II Study of Gemcitabine (GEM) and Weekly 48-Hour Continuous Infusion (CI) with High Dose 5-Fluorouracil (5-FU) in Advanced Exocrine Pancreatic Cancer (APC)," Proceedings of the Annual Meeting of the American Society of Clinical Oncology. vol. 18, p. 298 (1999) [ABSTRACT # 1145].

Romani et al. "Gastrin Receptor Antagonist CI-988 Inhibits Growth of Human Colon Cancer in Vivo and in Vitro," Aust. N.Z. J. Surgery. vol. 66 pp. 235-237 (1996).

Romani et al., "Potent new family of gastrin receptor antagonists (GRAs) produces in vitro and in vivo inhibition of human colorectal cancer (CRC) cell lines," Proceedings of the American Association for Cancer Research. vol. 35 p. 397 (1994) [ABSTRACT # 2369].

Rothenberg et al., "A phase II trial of gemcitabine in patients with 5-FU-refractory pancreas cancer," Annals of Oncology. vol. 7 pp. 347-353 (1996).

Scemama et al., "Characterisation of gastrin receptors on a rat pancreatic acinar cell line (AR42J). A possible model for studying gastrin mediated cell growth and proliferation," Gut. vol. 28, No. S1 pp. 233-236 (1987).

Scheele et al., "Indicators of prognosis after hepatic resection for colorectal secondaries," Surgery. vol. 110, No. 1 pp. 13-29 (1991).

Scheithauer et al., "Combined Intraperitoneal plus Intravenous cChemotherapy after Curative Resection for Colonic Adenocarcinome," European Journal of Cancer. vol. 31A, No. 12 pp. 1981-1986 (1995).

Schmitz et al., "CCK-B/gastrin receptors in human colorectal cancer," European Journal of Clinical Investigation. vol. 31 pp. 812-820 (2001).

Seitz et al., "Elevated Serum Gastrin Levels in Patients with Colorectal Neoplasia," J. Clin. Gastroenterol. vol. 13, No. 5 pp. 541-545 (1991).

Seva et al., "Characterization of the Glycine-Extended Gastrin (G-GLY) Receptor on AR4-2J Cells," Gastroenterology. p. A1005 (1995) [ABSTRACT].

Seva et al., "Lorglumide and Loxglumide Inhibit Gastrin-stimulated DNA Synthesis in a Rat Tumoral Acinar Pancreatic Cell Line (AR42J)," Cancer Research. vol. 50, No. 8 pp. 5829-5833 (1990).

Siemann, "Satisfactory and Unsatisfactory Tumor Models: Factors Influencing the Selection of a Tumor Model for Experimental Evaluation," Rodent Tumor Models in Experimental Cancer Therapy (Ed. Kallman) Pergamon Press, NY. pp. 12-15 (1987).

Singh et al., "Gut hormones in colon cancer: past and prospective studies," Cancer Journal. vol. 3, No. 1 pp. 28-33 (1990).

Singh et al., "High Levels of Progastrin Significantly Increase Premalignant Changes in Colonic Mucosa of Mice in Tesponse to the Chemical Carcinogen, AOM," Gastroenterology. vol. 114, No. 4 p. A680 (1998) [ABSTRACT # G2810].

Singh et al., "Incomplete processing of progastrin expressed by human colon cancer cells: roles of noncarboxyamidated gastrins," The American Physiological Society. pp. G459-G468 (1994).

Singh et al., "Novel Gastrin Receptors Mediate Mitogenic Effects of Gastrin and Processing Intermediates of Gastrin on Swiss 3T3 Fibroblasts. Absence of Detectable Cholecystokinin (CCK)-A and CCK-B Receptors," The Journal of Biological Chemistry. vol. 270, No. 15 pp. 8429-8438 (1995).

Singh et al., "Role of Gastrin and Gastrin Receptors on the Growth of a Transplantable Mouse Colon Carcinoma (MC-26) in BALB/c Mice," Cancer Research. vol. 46 pp. 1612-1616 (1986).

Smith et al., "Antisense oligonucleotides to gastrin inhibit growth of human pancreatic cancer," Cancer Letters. vol. 135 pp. 107-112 (1999).

Smith et al., "Elevated Gastrin Levels in Patients with Colon Cancer or Adenomatous Polyps," Digestive Diseases and Science. vol. 34, No. 2 pp. 171-174 (1989).

Sobhani et al., "Chronic Endogenous Hypergastrinemia in Humans: Evidence for a Mitogenic Effect on the Colonic Mucosa," Gastroenterology. vol. 105, No. 1 pp. 22-30 (1993).

Sobhani et al., "Immunohistochemical characterization of gastrinomas with antibodies specific to different fragments of progastrin," Gastroentérologie Clinique et Biologique. vol. 13, No. 11 pp. 865-872 (1989).

Soll et al. "Gastrin-Receptors on Isolated Canine Parietal Cells," The Journal of Clinical Investigation, Inc.. vol. 73 pp. 1434-1447 (1984).

Song et al., "The human gastrin/cholecystokinin type B receptor-gene: Alternative splice donor site in exon 4 generates two variant mRNAs," PNAS. vol. 90, No. 19 pp. 9085-9089 (1993).

Spitler, L.E. "Cancer Vaccines: The Interferon Analogy," Cancer Biotherapy. vol. 10, No. 1 pp. 1-3 (1995).

Stepan et al., "Glycine-Extended Gastrin Exerts Growth-Promoting Effects on Colon Cancer Cell Lines," Gastroenterology. vol. 110, No. 4 p. A1122 (1996) [ABSTRACT].

Stepan et al., "Glycine-Extended Gastrin Exerts Growth-Promoting Effects on Human Colon Cancer Cells," Molecular Medicine. vol. 5, No. 3 pp. 147-159 (1999).

Stubbs et al., "Correlation between Uptake of Labeled Anti-CCKB/Gastrin Receptor Antibodies and the Occurrence of Apoptosis in Hepatoma Cell Lines," Gastroenterology. vol. 122, No. 4, Suppl. 1 p. A-380 (2002) [ABSTRACT # T915].

Stubbs et al., "Endocytosis of Anti-CCK-B/Gastrin Receptor Antibody and Effect on Hepatoma Cell Lines," The Journal of Histochemistry & Cytochemistry. vol. 50, No. 9 pp. 1213-1217 (2002).

Takhar et al., "The role of gastrin in colorectal carcinogenesis," J.R. Coll. Surg. Edinb. Irel. vol. 2, No. 5 pp. 251-257 (2004).

Takinami et al., "YF476 is a new potent and selective gastrin/cholecystokinin-B receptor antagonist in vitro and in vivo," Ailment Pharmacol. Ther. vol. 11, No. 1 pp. 113-120 (1997).

Talley et al., "Risk for Colorectal Adenocarcinoma in Pernicious Anemia," Annals of Internal Medicine. vol. 111, No. 9 pp. 738-742 (1989).

Tang et al., "Expression of receptors for gut peptides in human pancreatic adenocarcinoma and tumor-free pancreas," British Journal of Cancer. vol. 75, No. 10 pp. 1467-1473 (1997).

Taniguchi et al., "Cholecystokinin-B/gastrin receptor signaling pathway involves tyrosine phosphorylations of $p125^{FAK}$ and $p42^{MAP}$," Oncogene. vol. 9 pp. 861-867 (1994).

Taylor, "Chemotherapy, radiotherapy and immunotherapy of colorectal neoplasia," Current Opinion in Gastroenterology. vol. 9 pp. 28-33 (1993).

Tielemans et al., "Proliferation of Enterochromaffinlike Cells in Omeprazole-Treated Hypergastrinemic Rats," Gastroenterology. vol. 96, No. 3 pp. 723-729 (1989).

Torosian et al., "Colon Carcinoma Metastatic to the Thigh—An Unusual Site of Metastasis. Report of a Case," Diseases of the Colon and Rectum. vol. 30, No. 10 pp. 805-808 (1987).

Tschmelitsch et al., "Enhanced Antitumor Activity of Combination Radioimmunotherapy ($^{131}$I-labeled Monoclonal Antibody A33) with Chemotherapy (Fluorouracil)," Cancer Research. vol. 57 pp. 2181-2186 (1997).

Ullrich et al. "Signal Transduction by Receptors with Tyrosine Kinase Activity," Cell. vol. 61 pp. 203-212 (1990).

UniProtKB/Swiss-Prot entry P01350, (1986) (accessed on Mar. 26, 2007).

Upp et al., "Polyamine Levels and Gastrin Receptors in Colon Cancers" Ann. Surg. vol. 207, No. 6 pp. 662-668 (1988).

Vaillant et al., "Cellular Origins of Different Forms of Gastrin. The Specific Immunocytochemical Localization of Related Peptides," The Journal of Histochemistry and Cytochemistry. vol. 27, No. 5 pp. 932-935 (1979).

Vaillant et al., "Repeat liver resection for recurrent colorectal metastasis," British J. Surgery. vol. 80, No. 3 pp. 340-344 (1993).

Van Solinge et al., "Expression but Incomplete Maturation of Progastrin in Colorectal Carcinomas," Gastroenterology. vol. 104 pp. 1099-1107 (1993).

Varro, A., and Dockray, G.J., "Post-translational processing of progastrin: inhibition of cleavage, phosphorylation and sulphation by brefeldin A," Biochem. J. vol. 295 pp. 813-819 (1993).

Varro et al., "Pathways of Processing of the Gastrin Precursor in Rat Antral Mucosa," Journal of Clinical Investigation. vol. 95 pp. 1642-1649 (1995).

Varro et al., "The human gastrin precursor," Biochem. J. vol. 256 pp. 951-957 (1988).

Vauthey et al., "Factors Affecting Long-Term Outcome After Hepatic Resection for Hepatocellular Carcinoma," The American Journal of Surgery. vol. 169 pp. 28-35 (1995).

Von Hoff, D.D., and Bearss, D., "New drugs for patients with pancreatic cancer," Curr. Opin. Oncology. vol. 14 pp. 621-627 (2002).

Wank "Cholecystokinin receptors," Am. J. Physiol. vol. 269 (Gastrointest. Liver Physiol.) pp. G628-G646 (1995).

Wank et al., "Brain and gastrointestinal cholecystokinin receptor family: Structure and functional expression," PNAS. vol. 89 pp. 8691-8695 (1992).

Wank et al., "Cholecystokinin Receptor Family. Molecular Cloning, Structure, and Functional Expression in Rat, Guinea Pig, and Human," Annals New York Academy of Sciences. vol. 713 pp. 49-66 (1994).

Watson, S.A., and Steele, R.J.C., "Gastrin antagonists in the treatment of gastric cancer," Anti-Cancer Drugs. vol. 4, No. 6 pp. 599-604 (1993).

Watson et al., "Detection of Gastrin Receptors on Gastrointestinal Tumours Using the Anti-Gastrin Receptor Monoclonal Antibody, 2CL," Gut. vol. 4 p. S68 (1993) [ABSTRACT # F271].

Watson et al., "Enhanced Inhibition of Pancreatic Cancer by Combination of the G17DT Immunogen and Gemcitabine," Amer. Soc. Clin. Oncol. vol. 37 (2002) [ABSTRACT].

Watson et al., "Expression of CCKB/Gastrin Receptor Isoforms in Gastro-intestinal Tumour Cells," Int. J. Cancer. vol. 77, No. 4 pp. 572-577 (1998).

Watson et al., "Gastrin: growth enhancing effects on human gastric and colonic tumour cells," British Journal of Surgery. vol. 75, No. 4 pp. 554-558 (1988).

Watson et al., "Gastrin Inhibition Increases the Potency of Cytotoxic Agents in Pancreatic Cancer," Gastroenterology. vol. 122, No. 4 p. A-241 (2002) [ABSTRACT # M952].

Watson et al., "Synergistic inhibitory effects of G17DT on gastrointestinal tumour growth in combination with cytotoxic agents," Proc. Am. Soc. Clin. Oncol. vol. 22 (2003) [ABSTRACT # 3497].

Watson et al., "The Effect of the E2 Prostaglandin Enprostil, and the Somatostatin Analogue SMS 201 995, on the Growth of a Human Gastric Cell Line, MKN45G," Int. J. Cancer. vol. 45 pp. 90-94 (1990).

Weinberg et al., "Cholecystokinin A and B Receptors Are Differentially Expressed in Normal Pancreas and Pancreatic Adenocarcinoma," The Journal of Clinical Investigation. vol. 100, No. 3 pp. 597-603 (1997).

Weiner, L.M., "An Overview of Monoclonal Antibody Therapy of Cancer," Seminars in Oncology. vol. 26, No. 4, Suppl. 12 pp. 41-50 (1999).

Weinstock et al., "Binding of Gastrin$_{17}$ to Human Gastric Carcinoma Cell Lines," Cancer Research. vol. 48, No. 4 pp. 932-937 (1988).

Wendlberger et al, "The syntheses of human big gastrin I and its 32-leucine analog," Chemical Abstracts. vol. 92, No. 21 p. 722 (1980) [ABSTRACT 92:198749s].

Wong et al., "Postprandial hypergastrinaemia in patients with colorectal cancer," Gut. vol. 32 pp. 1352-1354 (1991).

Wunsch, E., and Moroder, L., "Biological and Immunological Properties of Human Gastrin I Analogues," Hoppe-Syeler's Z. Physiol. Chem. vol. 363 pp. 665-669 (1982).

Yamaguchi et al., "Amino-terminal immunoreactivity of big gastrin in plasma and tumors obtained from patients with Zollinger-Ellison Syndrome," Chem. Abstracts. vol. 100 p. 373 (1984) [ABSTRACT # 100:154661m].

Yanaihara et al. "A New Type of Gastrin Derivative and its Use for Production of Central Region-Specific Anti-Gastrin Sera," Biomedical Research. vol. 1 pp. 242-247 (1980).

Yuki et al., "YM022, A Potent and Selective Gastrin/CCK-B Receptor Antagonist, Inhibits Peptone Meal-Induced Gastric Acid Secretion in Heidenhain Pouch Dogs," Digestive Diseases and Sciences. vol. 42, No. 4 pp. 707-714 (1997).

"ADAP drugs: leucovorin," Access Project, http://www.aegis.com/factshts/network/access/drugs/leuc.html (1996) (accessed on Aug. 13, 2004), 1 page.

Aphton Biopharma BIO2005 Presentation, Jun. 19-22, Philadelphia, PA (2005), 26 pages.

Baba et al., "Glycine-Extended Gastrin Induces Matrix Metalloproteinase-1- and—3-Mediated Invasion of Human Colon Cancer Cells Through Type 1 Collagen Gel and Matrigel," International Journal of Cancer. vol. 111, No. 1 pp. 23-31 (2004).

Belani, C., "Paclitaxel and Docetaxel Combinations in Non-Small Cell Lung Cancer," Chest. vol. 117 pp. 144S-151S (2000).

Bentley et al., "Human Gastrin: Isolation, Structure and Synthesis," Nature. vol. 209, No. 5023 pp. 583-585 (1966).

Bock et al., "Benzodiazepine Gastrin and Brain Cholecystokinin Receptor Ligands: L-365,260," Journal of Medicinal Chemistry. vol. 32, No. 1 pp. 13-16 (1989).

Bold et al., "Gastrin Stimulates Growth of Human Colon Cancer Cells Via A Receptor Other Than CCK-A or CCK-B," Biochemical and Biophysical Research Communications. vol. 202, No. 3 pp. 1222-1226 (1994).

Brett et al., "Lymphocyte Expression of the CCK-B/Gastrin Receptor (CCK-BR) in Gastric Lymphomas, *Helicobacter pylori* Gastritis and Normal Gastric Biopsies," Gastroenterology. vol. 114, No. 4, Suppl. 1 p. A57 (1998) [ABSTRACT # G2333].

Brett et al., "The Effect of Antibodies Raised Against Gastrimmune on the Proliferation of Human Pancreatic Carcinoma Cell Lines," Gut. vol. 42 p. A26 (1998) [Abstract #W190].

Bruns et al., "Therapy of Human Pancreatic Carcinoma Implants by Irinotecan and the Oral Immunomodulator JBT 3002 Is Associated with Enhanced Expression of Inducible Nitric Oxide Synthase in Tumor-infiltrating Macrophages," Cancer Research. vol. 60 pp. 2-7 (2000).

Caplin et al., "Expression and Processing of Gastrin in Patients with Pancreatic Carcinoma," Gastroenterology. vol. 114, Suppl. 1 p. A445 (1998) [ABSTRACT #G1809].

Caplin et al., "The CCK-B/Gastrin Receptor in Hepatocellular Carcinoma," Gastroenterology. vol. 110, No. 4 p. A1162 (1996) [ABSTRACT].

Certified English Translation of PCT Patent Application No. WO2001/13114 "Use of stabilized synthetic compounds in immunoassay.", publication date Feb. 22, 2001.

"Clinical Trial Initiated with Chemorefractory Patients," Cancer Weekly, The Gale Group, (Jan. 9, 2001).

"Clinical trials update," Scrip, Informa UK Ltd., No. 2547 p. 25 (Jun. 9, 2000).

de Weerth et al., "Human Pancreatic Cancer Cell Lines Express the $CCK_b$ Receptor," Hepato-Gastroenterology. vol. 46 pp. 472-478 (1999).

de Weerth et al., "Human Pancreatic Cancer Cell Lines Express the $CCK_B$/Gastrin Receptor," Gastroenterology. vol. 106, No. 4 p. A289 (1994) [ABSTRACT].

Dufresne et al., "Cholecystokinin and Gastrin Receptors," Physiol. Rev. vol. 86 pp. 805-847 (2006).

Edgington, "Biotech Vaccines' Problematic Promise," Bio/Technology. vol. 10 pp. 763-766 (1992).

Evans, "Chemotherapy in Advanced Non-Small Cell Lung Cancer," 37th Annual Meeting of the American Society of Clinical Oncology, Day 1, May 22, 2001, meeting report published by Medscape.

Fennerty, "Updated on Barrett's Esophagus" Digestive Diseases Week, May 22, 2001, meeting report published by Medscape, www.medscape.com, 6 pages.

Festen et al., "Effect of Oral Omeprazole on Serum Gastrin and Serum Pepsinogen I Levels," Gastroenterology. vol. 87, No. 5 pp. 1030-1034 (1984).

Fields, "Preparation of Antipeptide Antibodies: Introduction to Peptide Synthesis," Current Protocols in Molecular Biology. 11.15.1-11.15.9 (2002).

Freston, "Long-Term Acid Control and Proton Pump Inhibitors: Interactions and Safety Issues in Perspective," American Journal of Gastroenterology. vol. 92, No. 4 pp. 51S-57S (1997).

Gil-Delgado et al., "Prospective Phase II Trial of Irinotecan, 5-Fluorouracil, and Leucovorin in Combinations as Salvage Therapy for Advanced Colorectal Cancer," American Journal of Clinical Oncology. vol. 24, No. 1 pp. 101-105 (2001).

Grabowska, A., and Watson, S.A., "Downregulation of the Gastrin Gene Using Small Interfering RNA," Regulatory Peptides. vol. 122, No. 1 p. 46 (2004) [ABSTRACT # A150].

Gutman et al., "Accelerated Growth of Human Colon Cancer Cells in Nude Mice Undergoing Liver Regeneration," Invasion and Metastasis. Vol. 14, Nos. 1-6 pp. 362-371 (1994-95).

Harris et al., "The Biological and Therapeutic Importance of Gastrin Gene Expression in Pancreatic Adenocarcinomas," Cancer Research. vol. 64 pp. 5624-5631 (2004).

Harrison et al. "The Effect of the Gastrin Receptor Antagonist Proglumide on Survival in Gastric Carcinoma," Cancer. vol. 66, No. 7 pp. 1449-1452 (1990).

He at al., "Biological Activity and Ferric Ion Binding of Fragments of Glycine-Extended Gastrin," Biochemistry. vol. 43, No. 37 pp. 11853-11861 (2004).

Heinemann et al., "Cellular Elimination of 2',2'-Diflourodeoxycytidine 5'-Triphosphate: A Mechanism of Self-Potentiation," Cancer Research. vol. 52 pp. 533-539 (1992).

Huang et al., "Termination of DNA Synthesis by 9-β-D-Arabinofuranosyl-2-fluoroadenine," The Journal of Biological Chemistry. vol. 265, No. 27 pp. 16617-16625 (1990).

Ikeda et al., "Preliminary report of tumor metastasis during liver regeneration after hepatic resection in rats," European Journal of Surgical Oncology. vol. 21, No. 2 pp. 188-190 (1995).

International Preliminary Examination Report corresponding to International Patent Application No. PCT/US2002/021768 dated Feb. 9, 2004.

International Preliminary Report on Patentability corresponding to International Patent Application No. PCT/US2005/010532 dated Nov. 3, 2006.

Issued Patent corresponding to Australian Patent Application No. 2005228897 dated Mar. 25, 2010.

Iwao et al., "Effects of Omeprazole and Lansoprazole on Fasting and Postprandial Serum Gastrin and Serum Pepsinogen A and C," Hepato-Gastroenterology. vol. 42 pp. 677-682 (1995).

Justin et al., "Gastric Acid Suppression Using Anti-Gastrin-17 Antibodies Produced by a Gastrin Immunogen, Gastrimmune, in an in Vivo Pig Model," Gastroenterology. vol. 108, No. 4 p. A125 (1995) [ABSTRACT].

Kipriyanov, S.M., and Little, M., "Generation of Recombinant Antibodies," Molecular Biotechnology. vol. 12 pp. 173-201 (1999).

Koelz, "Treatment of Reflux Esophagitis with $H_2$-Blockers. Antacids and Prokinetic Drugs. An Analysis of Randomized Clinical Trials," Scandinavian Journal of Gastroenterology. Supplement 156 pp. 25-36 (1989).

Koh et al., "Glycine-Extended Gastrin Promotes the Growth of a Human Hepatoma Cell Line," Gastroenterology. vol. 110, No. 4 p. A1089 (1996) [ABSTRACT].

Kohler et al., "Continuous cultures of fused cells secreting antibody of predefined specificity," Nature. vol. 256 pp. 495-497 (1975).

Kothary, P.C., and Lvinik, A., "$NH_2$-Terminal of Gastrin-17 in Duodenal Ulcer Disease: Identification of Progastrin-17," Biochemical and Biophysical Research Communications. vol. 146, No. 2 pp. 884-888 (1987).

Kuipers et al., "The Efficacy and Safety of Long-term Omeprazole Treatment for Gastroesophageal Reflux Disease," Gastroenterology. vol. 118, No. 4 pp. 795-798 (2000).

Laurie, S.A., and Kris, M.G., "Single-Agent Docetaxel (Taxotere) in the Treatment of Advanced Non-Small-Cell Lung Cancer: Clinical Concepts and Commentary," Clinical Lung Cancer. vol. 1, Suppl 1 pp. S5-S9 (2000).

Lawrence et al., "Radiosensitization of Pancreatic Cancer Cells by 2',2'-Difluoro-2'-Deoxycytidine," Int. J. Radiation Oncology Biol. Phys. vol. 34, No. 4 pp. 867-872 (1996).

Le Meuth et al., "Differential Expression of A- and B-Subtypes of Cholecystokinin/Gastrin-Receptors in the Developing Calf Pancreas," Endocrinology. vol. 133, No. 3 pp. 1182-1191 (1993).

Ledda-Columbano et al., "Compensatory Regeneration, Mitogen-Induced Liver Growth, and Multistage Chemical Carcinogenesis," Environmental Health Perspectives. vol. 101, No. 5 pp. 163-168 (1993).

Leith et al., "Effects of Partial Hepatectomy on Growth Characteristics and Hypoxic Fractions of Xenografted DLD-2 Human Colon Cancers," Radiation Research. vol. 123, No. 2 pp. 263-268 (1992).

Li et al., "Induction of growth inhibition and apoptosis in pancreatic cancer cells by auristatin-PE and gemcitabine," International Journal of Molecular Medicine. vol. 3 pp. 647-653 (1999).

Machine translation of JP 06107564.

MacKenzie et al., "Development of a Radioligand Binding Assay to Characterise Gastrin Receptors in the Human Gastrointestinal Tract," Gut. vol. 38, Suppl. 1 p. A37 (1996) [ABSTRACT # T146].

McCloy et al., "Pathophysiological Effects of Long-Term Acid Suppression in Man," Digestive Diseases and Sciences. vol. 40, No. 2 pp. 96S-120S [Supplement] (1995).

McRae et al., "Role of Gastrin and Gastrin Receptors in the Growth of Human Colon Carcinoma Cells," The Journal of Cell Biology. vol. 103, No. 5, Part 2 p. 22a (1986) [Abstract # 74].

Notice of Acceptance corresponding to Australian Patent Application No. 2004225437 dated Apr. 29, 2010.

Notice of Allowance corresponding to Japanese Patent Application No. 2006-509465 dated Jan. 18, 2011.

Notice of Allowance corresponding to U.S. Appl. No. 10/813,336 dated May 15, 2006.

Notice of Allowance corresponding to U.S. Appl. No. 10/813,336 dated Oct. 3, 2006.

Official Action corresponding to Canadian Patent Application No. 2,520,010 dated Nov. 1, 2010.

Official Action corresponding to Canadian Patent Application No. 2,561,405 dated Nov. 3, 2010.

Official Action corresponding to European Patent Application No. 02 721 529.2-2107 dated Sep. 23, 2004.

Official Action corresponding to European Patent Application No. 04 758 568.2-2404 dated Jul. 17, 2007.

Official Action corresponding to European Patent Application No. 05 730 336.4-1222 dated Apr. 27, 2007.

Official Action corresponding to Indian Patent Application No. 2441/CHENP/2005 dated Jul. 24, 2007.

Official Action corresponding to Indian Patent Application No. 6318/DELNP/2006/707 dated Jul. 5, 2010.

Official Action corresponding to Japanese Patent Application No. 2007-506474 dated Jun. 1, 2010.

Official Action corresponding to U.S. Appl. No. 08/219,773 dated Oct. 19, 1994.

Official Action corresponding to U.S. Appl. No. 08/285,984 dated Feb. 7, 1995.

Official Action corresponding to U.S. Appl. No. 08/465,917 dated Aug. 12, 1996.

Official Action corresponding to U.S. Appl. No. 10/104,607 dated Mar. 29, 2005.

Official Action corresponding to U.S. Appl. No. 10/104,607 dated Nov. 21, 2005.

Official Action corresponding to U.S. Appl. No. 10/192,257 dated Sep. 21, 2005.

Official Action corresponding to U.S. Appl. No. 10/762,226 dated Dec. 27, 2006.

Official Action corresponding to U.S. Appl. No. 11/663,126 dated Jun. 22, 2009.

Official Action corresponding to U.S. Appl. No. 11/663,126 dated Nov. 25, 2009.

Official Action corresponding to U.S. Appl. No. dated 11/663,126 dated Jun. 2, 2010.

Official Action corresponding to U.S. Appl. No. 11/499,261 dated Mar. 15, 2007.

Ohsawa et al., "Effects of Three $H_2$-Receptor Antagonists (Cimetidine, Famotidine, Ranitidine) on Serum Gastrin Level," International Journal of Clinical Pharmacology Research. vol. 22, No. 2 pp. 29-35 (2002).

"Other News to Note," Bioworld Today, American Health Consultants Inc., vol. 11, No. 82. pp. 1-8 (Apr. 27, 2000).

PalnØs Hansen et al., "Metabolism and Influence of Glycine-Extended Gastrin on Gastric Acid Secretion in Man," Digestion. vol. 57 pp. 22-29 (1996).

Pauwels et al., "Identification of Progastrin in Gastrinomas, Antrum, and Duodenum by a Novel Radioimmunoassay," The Journal of Clinical Investigation. vol. 77 pp. 376-381 (1986).

"*Prilosec* OTC Review: Two Advisory Committee Members Weigh in Without Voting," The Pink Sheet. pp. 22-23 (2002).

Reddy, "Small Cell Lung Cancer: Improving Outcomes," American Society for Therapeutic Radiology and Oncology, $42^{nd}$ Annual Meeting, Day 1, Oct. 22, 2000, meeting report published by Medscape.

Rehfeld, "The New Biology of Gastrointestinal Hormones," Physiological Reviews. vol. 78, No. 4 pp. 1087-1108 (1998).

Ritter et al., "Serological Analysis of Human Anti-Human Antibody Responses in Colon Cancer Patients Treated with Repeated Doses of Humanized Monoclonal Antibody A33," Cancer Research. vol. 61 pp. 6851-6859 (2001).

Schlom, "Monoclonal Antibodies: They're More and Less Than You Think," Molecular Foundations of Oncology. ed. Broder Williams & Williams, Baltimore MD, pp. 95-134 (1991).

Senior, "Immunization blocks gastrin's ability to promote tumour cell division," Drug Discovery Today. vol. 6, No. 2 pp. 62-63 (2001).

Shewach, D.S., and Lawrence, T.S., "Radiosensitization of Human Solid Tumor Cell Lines With Gemcitabine," Seminars in Oncology. vol. 23, No. 5, Suppl. 10 pp. 65-71 (1996).

Shewach et al., "Metabolism of 2',2'-Difluoro-2'-Deoxycytidine and Radiation Sensitization of Human Colon Carcinoma Cells," Cancer Research. vol. 54 pp. 3218-3223 (1994).

Slooter et al., "Tumor growth stimulation after partial hepatectomy can be reduced by treatment with tumor necrosis factor α," British Journal of Surgery. vol. 82 pp. 129-132 (1995).

Smith, J.P., and Solomon, T.E., "Effects of Gastrin, Proglumide, and Somatostatin on Growth of Human Colon Cancer," Gastroenterology. vol. 95, No. 6 pp. 1541-1548 (1988).

Smith et al., "Sensitivity of the Esophageal Mucosa to pH in Gastroesophageal Reflux Disease," Gastroenterology. vol. 96 pp. 683-689 (1989).

Sundler et al., "The Neuroendocrine System of the Gut—An Update," Acta Oncologica. vol. 30, No. 4 pp. 419-427 (1991).

Trakal et al., "Diagnosis and Etiology of Barrett's Esophagus: Presence of Gastrin Secreting Cells," Acta Gastroenterológica Latinoamericana. vol. 15, No. 2 pp. 67-80 (1985) [ABSTRACT], Abstract only.

Upp et al., "Clinical Significance of Gastrin Receptors in Human Colon Cancers" Cancer Research. vol. 49 pp. 488-492 (1989).

Watson et al., "Growth-promoting action of gastrin on human colonic and gastric tumour cells cultured in vitro," British Journal of Surgery. vol. 75, No. 4 pp. 342-345 (1988).

Wetscher et al., "Pathophysiology of Gastroesophageal Reflux Disease," R.A. Heinder ed., R.G. Landes Co., Chapter 2 pp. 7-29 (1993).

Zeitoun, "Comparison of Omeprazole with Ranitidine in the Treatment of Reflux Oesophagitis," Scand. J. Gastroenterol. vol. 24, Suppl. 166 pp. 83-87 (1989).

Zeng et al., "Localization of PACAP Receptors on Rat Fundic ECL and D Cells," Gastroenterology. vol. 110, Suppl. 4 p. A1136 (1996) [ABSTRACT].

Zhou et al., "Pre- and Postoperative Sequential Study on the Serum Gastrin Level in Patients with Lung Cancer," Journal of Surgical Oncology. vol. 51 pp. 22-25 (1992).

\* cited by examiner

Representative Total Gastrin 17 calibration curve

Representative free gastrin 17 calibration curve

SEQUENCE LISTING

<160> NUMBER OF SEQ ID NOS: 8

<210> SEQ ID NO 1
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (17)..(17)
<223> OTHER INFORMATION: AMIDATION

<400> SEQUENCE: 1

```
Glu Gly Pro Trp Leu Glu Glu Glu Glu Ala Tyr Gly Trp Met Asp
1               5                   10                  15

Phe

<210> SEQ ID NO 2
<211> LENGTH: 18
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 2

Glu Gly Pro Trp Leu Glu Glu Glu Glu Ala Tyr Gly Trp Met Asp
1               5                   10                  15

Phe Gly

<210> SEQ ID NO 3
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: MOD_RES
<222> LOCATION: (34)..(34)
<223> OTHER INFORMATION: AMIDATION

<400> SEQUENCE: 3

Glu Leu Gly Pro Gln Gly Pro Pro His Leu Val Ala Asp Pro Ser Lys
1               5                   10                  15

Lys Glu Gly Pro Trp Leu Glu Glu Glu Glu Ala Tyr Gly Trp Met
            20                  25                  30

Asp Phe

<210> SEQ ID NO 4
<211> LENGTH: 35
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 4

Glu Leu Gly Pro Gln Gly Pro Pro His Leu Val Ala Asp Pro Ser Lys
1               5                   10                  15

Lys Glu Gly Pro Trp Leu Glu Glu Glu Glu Ala Tyr Gly Trp Met
            20                  25                  30

Asp Phe Gly
        35

<210> SEQ ID NO 5
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID
```

```
<400> SEQUENCE: 5

Glu Gly Pro Trp Leu Glu
1               5

<210> SEQ ID NO 6
<211> LENGTH: 9
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: AMIDATION

<400> SEQUENCE: 6

Glu Glu Ala Tyr Gly Trp Met Asp Phe
1               5

<210> SEQ ID NO 7
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 7

Glu Leu Gly Pro Gln Gly
1               5

<210> SEQ ID NO 8
<211> LENGTH: 7
<212> TYPE: PRT
<213> ORGANISM: Homo sapiens

<400> SEQUENCE: 8

Tyr Gly Trp Met Asp Phe Gly
1               5
```

GASTRIN HORMONE IMMUNOASSAYS

RELATED APPLICATIONS

This application is a continuation of U.S. application Ser. No. 10/813,336, now U.S. Pat. No. 7,235,376, to Stephen Grimes, John Little, and Lorraine McLoughlin, filed on Mar. 29, 2004, entitled "GASTRIN HORMONE IMMUNOASSAYS", which claims the benefit of priority under 35 U.S.C. §119(e) to U.S. Provisional Application Ser. No. 60/458,244 to Stephen Grimes, John Little and Lorraine McLoughlin, filed on Mar. 28, 2003, entitled "GASTRIN HORMONE ASSAY". This application also is related to U.S. Provisional Application No. 60/557,759 to Stephen Grimes and Ronald Makishima, filed on Mar. 29, 2004. The subject matter of each of these applications is incorporated by reference in its entirety.

FIELD OF THE INVENTION

The invention relates to ELISA methods for detecting and/or quantifying a biological peptide, particularly gastrin hormone peptides, in a biological fluid. In particular, the invention relates to methods for detecting and/or quantifying free peptide, and total peptide including antibody-bound peptide in a biological fluid.

BACKGROUND OF THE INVENTION

Although gastrin hormone was first identified one hundred years ago, and was purified in the 1960's, its effects on different tissues in normal and disease tissues is still incompletely understood. One major reason for this gap in knowledge of the gastrin system has been the difficulty in separately detecting and quantifying each of the several forms of gastrin hormone.

In mammals the peptide hormone, gastrin exists in several forms, grouped into two major size classes, "little" gastrin and "big" gastrin, on the basis of the number of amino acid residues in the peptide chain. The "little" gastrin form includes mature gastrin-17 (G17) and glycine-extended G17 (G17-Gly); and "big" gastrin includes gastrin-34 (G34) and glycine-extended G34 (G34-Gly). The mature form of G17 is a major effector of stomach acid secretion and is estimated to be about six times more effective in this role than is G34. The various forms of gastrin are produced in vivo from a precursor peptide, progastrin, by cleavage and in some cases, modification of the cleaved form. Human G34 has the entire seventeen amino acid sequence of G17 at its C-terminal, and, predictably, cross-reacts immunologically with G17.

Mature G17 is modified at both amino- and carboxy-terminal residues: the N-terminal glutamic acid is cyclized to form pyroglutamic acid (pGlu) and the free carboxyl group of the C-terminal phenylalanine residue is amidated by the enzyme, peptidyl α-amidating mono-oxygenase (PAM) to form a C-terminal Phe-$NH_2$. (See Dockray et al., Ann. Rev. Physiol. (2001) 63: 119-139).

Mature G17, the predominant form of "little" gastrin in humans, has the amino acid sequence: pEGPWLEEEEEAYGWMDF-$NH_2$ (SEQ ID NO: 1). G17-Gly is an incompletely processed form of gastrin found as a minor component of "little" gastrin in healthy human subjects and has the amino acid sequence: pEGPWLEEEEEAYGWMDFG (SEQ ID NO: 2).

Gastrin-34, the predominant form of "big" gastrin in humans, has the amino acid sequence: pELGPQGPPHL-VADPSKKEGPWLEEEEEAYGWMDF-$NH_2$ (SEQ ID NO: 3), and glycine-extended gastrin 34 (G34-Gly), has an extra C-terminal glycine residue, having the amino acid sequence: pELGPQGPPHLVADPSKKEGPWLEEEEEAYGWMDFG (SEQ ID NO: 4).

Gastrin is secreted by the pyloric antral-G cells of the stomach in response to gastrin-releasing peptide (GRP). Gastrin secretion is suppressed by gastric acid and the paracrine action of several peptide hormones, most notably, somatostatin. It has long been recognized that gastrin peptides function to stimulate acid secretion in the stomach of healthy individuals, however, it has only recently been shown that these peptides also control proliferation, differentiation and maturation of different cell types in the gastrointestinal (GI) system.

In addition to their local activity in the GI system, G17 and, to a lesser extent, G17-Gly are released into the bloodstream and have been found to increase in the serum of patients afflicted with gastrointestinal disorders and diseases, such as gastric cancer, colorectal cancer, and pancreatic cancer. These gastrin species have more recently also been found to be associated with other diseases not associated with the gastrointestinal tract, including small cell lung cancer (SCLC) and liver metastasized tumors. See for example "*Gastrin and Colon Cancer: a unifying hypothesis*" S. N. Joshi et al., Digestive Diseases (1996) 14: 334-344; and "*Gastrin and colorectal cancer*" Smith, A. M. and Watson, S. A. Alimentary Pharmacology and Therapeutics (2000) 14(10): 1231-1247.

Antibodies are key reagents in numerous assay techniques used in medical, veterinary and other fields. Such tests include many routinely used immunoassay techniques, such as for example, enzyme-linked immunosorbant assays (ELISA), radioimmunoassays (RIA), immunohistochemistry (IHC), and immunofluorescence (IF) assays.

Monoclonal antibodies (MAbs) have unique characteristics that render them superior in many respects to polyclonal antisera and to antibodies purified from polyclonal antisera when used in many of these assays. These attributes include monodeterminant specificity for the target antigen (i.e. specificity for a single epitope), unchanging specificity among different antibody preparations, as well as unchanging affinity and chemical composition over time. Furthermore, MAbs can be produced indefinitely and in unlimited amounts by in vitro methods. These properties are in sharp contrast to those of polyclonal antibodies, which require in vivo immunization methods with the unavoidable associated biological variability and limited antibody production capacity over the lifespan of the immunized animal.

Despite these advantages, differences exist between individual MAbs even though they may be specific for the same epitope. For example, differences between MAbs induced by immunization with a single antigenic epitope region can arise with respect to any or all of the following characteristics: 1) the fine specificity for the molecular composition and tertiary structure of the epitope; 2) the antibody idiotype; 3) the antibody affinity; 4) the antibody allotype; and 5) the antibody isotype. These characteristic differences can affect the behavior of MAbs in a particular immunoassay, such that different MAb isolates raised against the same antigenic region can behave differently in a given assay. Consequently, some MAbs will be superior to others that bind the same epitope when used as reagents in a particular immunoassay.

The immunoassay may be an enzyme-linked immunosorbent assay (ELISA) or a radioimmunoassay (RIA), an immuno-detection assay, such as an ELISPOT, slot-blot, and western blot. As a general guide to such techniques, see for instance, Ausubel et al. (eds) (1987) in "*Current Protocols in Molecular Biology*" John Wiley and Sons, New York, N.Y.

Alternatively, the immunoassay may be an immunohistochemical (IHC) staining or immunofluorescence (IF) procedure for visualization of a gastrin hormone in a tissue sample. See for example "*Principles and Practice of Immunoassay*" (1991) Christopher P. Price and David J. Neoman (eds), Stockton Press, New York, N.Y.

Monoclonal antibodies specific for the N-terminal region and the C-terminal region of G17 have been described. See for example, Azuma et al., *Gastroenterologica Japonica* (1986) 21(4): 319-324; Ohning et al., *Peptides* (1994) 15(3): 417-423; Fuerle et al., *Pancreas* (1995) 10(3):281-286; Kovacs et al., *Peptides* (1996) 17 (4): 583-587; Ohning et al., *Am. J Physiol*. (1996) 271(3 Pt 1):G470-476; Sipponen et al., (2002) Scand. J. Gastroenterol. 37(7): 785-791. However, none of these antibodies were shown, either alone or in combination, to be capable of distinguishing and quantifying each of the forms of gastrin hormone found in biological fluids in normal and disease states.

Anti-gastrin polyclonal antibodies have been shown to be effective in inhibiting gastrin activity ("Inhibition of gastrin activity by incubation with antibodies to the C-terminal tetrapeptide of gastrin" Jaffe et al., *Surgery* (1969) 65(4):633-639); and non-human anti-gastrin polyclonal antibodies have been applied to therapy in a patient suffering from Zollinger-Ellison syndrome, a pathological condition in which excessive gastrin is produced without stimulation by feeding. See Hughes et al., "*Therapy with Gastrin Antibody in the Zollinger-Ellison Syndrome*" Hughes et al., *Digestive Diseases* (1976) 21(3):201-204. However, these rabbit anti-gastrin antibodies had "at best a short term effect in this patient." (Hughes at p. 204).

Recently, the ratio of amidated to non-amidated gastrin hormone in serum has been suggested as providing an indication of an individual's risk profile for developing duodenal ulcer disease or gastric atrophy. See U.S. patent Publication No. 2003/0049698 entitled "Diagnosis and Treatment of Gastrointestinal Disease" of T. C. Wang.

Until now, MAbs capable of sensitively detecting, and accurately distinguishing each of the G17, G17-Gly, G34, and G34-Gly forms of gastrin hormone have not been available. Furthermore, until the present invention, it was not possible to accurately measure the amounts of each of these forms of gastrin hormone in a sample of biological fluid. Use of the Mabs of the invention in assays for clinical testing more precisely defines the biology of gastrin hormone in normal and disease states and to provides MAb compositions for pharmaceutical use and methods for the prevention and treatment of gastrin-associated diseases and conditions.

SUMMARY OF THE INVENTION

The present invention provides a method for determining the total amount of gastrin hormone including the antibody-bound and free in a biological fluid sample. The method includes the steps of: (a) obtaining a biological fluid sample comprising a gastrin hormone from a patient; (b) providing an immobilized antibody that selectively binds a C-terminal epitope of the gastrin hormone; (c) incubating the sample in the presence of an N-terminal sequence gastrin peptide under suitable conditions for binding of the gastrin hormone in the sample to said antibody to produce an immobilized complex of said antibody bound to the gastrin hormone; (d) washing the immobilized complex to remove N-terminal sequence gastrin peptide, and incubating the complex with a suitable detectable marker-conjugated antibody that selectively binds an N-terminal epitope of gastrin hormone to form an immobilized detectable marker-conjugated antibody complex; (e) washing the immobilized detectable marker-conjugated antibody complex, and incubating with a development reagent; and (f) measuring the developed reagent to determine the total amount of the gastrin hormone in the biological fluid sample.

The invention also provides a method for determining the amount of free gastrin hormone in a biological fluid sample. The method includes the steps of: (a) obtaining a biological fluid sample comprising a gastrin hormone from a patient; (b) providing an immobilized antibody that selectively binds a N-terminal epitope of the gastrin hormone; (c) incubating the sample under suitable conditions for binding of the gastrin hormone in the sample to said antibody to produce an immobilized complex of said antibody bound to the gastrin hormone; (d) washing the immobilized complex to remove unbound components, including said antibody, and reacting the complex with a suitable detectable marker-conjugated antibody that selectively binds an C-terminal epitope bound to the gastrin hormone; (e) washing the immobilized detectable marker-conjugated antibody complex, and incubating with a development reagent; and (f) measuring the developed reagent to determine the amount of free gastrin hormone in the biological fluid sample.

The invention further provides a method for determining the total amount of bound plus free peptide in a biological fluid sample, wherein at least a portion of the peptide is reversibly bound at a first binding sequence. The method includes the following steps: (a) obtaining a biological fluid sample containing the peptide; (b) providing a solid substrate coated with an antibody that selectively binds a first epitope of the peptide which is not present in the first binding sequence; (c) incubating a portion of the sample in the presence of a fragment of the peptide comprising the first binding sequence, but not the first epitope, under suitable conditions for binding of the peptide to said antibody to produce a complex of said antibody bound to the peptide; (d) washing the wells to remove unbound antibody and the fragment of the peptide, and reacting the complex with a suitable detectable marker-conjugated antibody that selectively binds a second epitope of the peptide; (e) washing the wells, and adding a development reagent to the wells; and (f) measuring the developed reagent to determine the total amount of bound plus free peptide in the biological fluid sample.

The invention also provides a method of evaluating a gastrin hormone blocking treatment of a patient suffering from a gastrin hormone-mediated disease or condition. The method includes the steps of: a) obtaining a first sample of biological fluid from the patient prior to or in the early stages of a treatment; b) determining the level of gastrin hormone in the first sample by an immunoassay method; c) performing a diagnosis on the basis of the disease or condition to be treated and the level of gastrin hormone in the first sample; d) administering a treatment to the patient, comprising: a first agent or a substance that generates a first agent which binds gastrin hormone so as to modulate its binding to its target receptor in vivo; e) obtaining a second sample of biological fluid from the patient after a suitable time within which the treatment would have an effect; f) determining the level of total gastrin hormone including bound and free gastrin hormone in a first aliquot of the second sample by an immunoassay method, wherein the first aliquot of the second sample is incubated with (i) a second agent that displaces any gastrin hormone bound by the first agent, and (ii) an immobilized anti-gastrin hormone antibody, wherein the immobilized antibody does not bind the second agent; washing to remove the second agent and adding a detectable antibody that binds the gastrin hormone and does not compete with the immobilized antibody, forming an immunocomplex comprising the immobilized antibody bound to gastrin hormone, the gastrin hormone in turn being bound by the detectable antibody; g) detecting the amount of the detectable antibody in the immunocomplex and thereby determining the amount of total gastrin hormone in the second sample; h) determining the level of free gastrin hormone by repeating steps f) and g) with a second aliquot of the second sample, wherein the incubation in step f) is performed without the second agent; and j) comparing the determined amounts of free gastrin hormone in the first sample with the amounts of free and total gastrin hormone in the second sample so as to determine the efficacy of the gastrin blocking treatment in the patient.

DETAILED DESCRIPTION OF THE INVENTION

Figure 1:
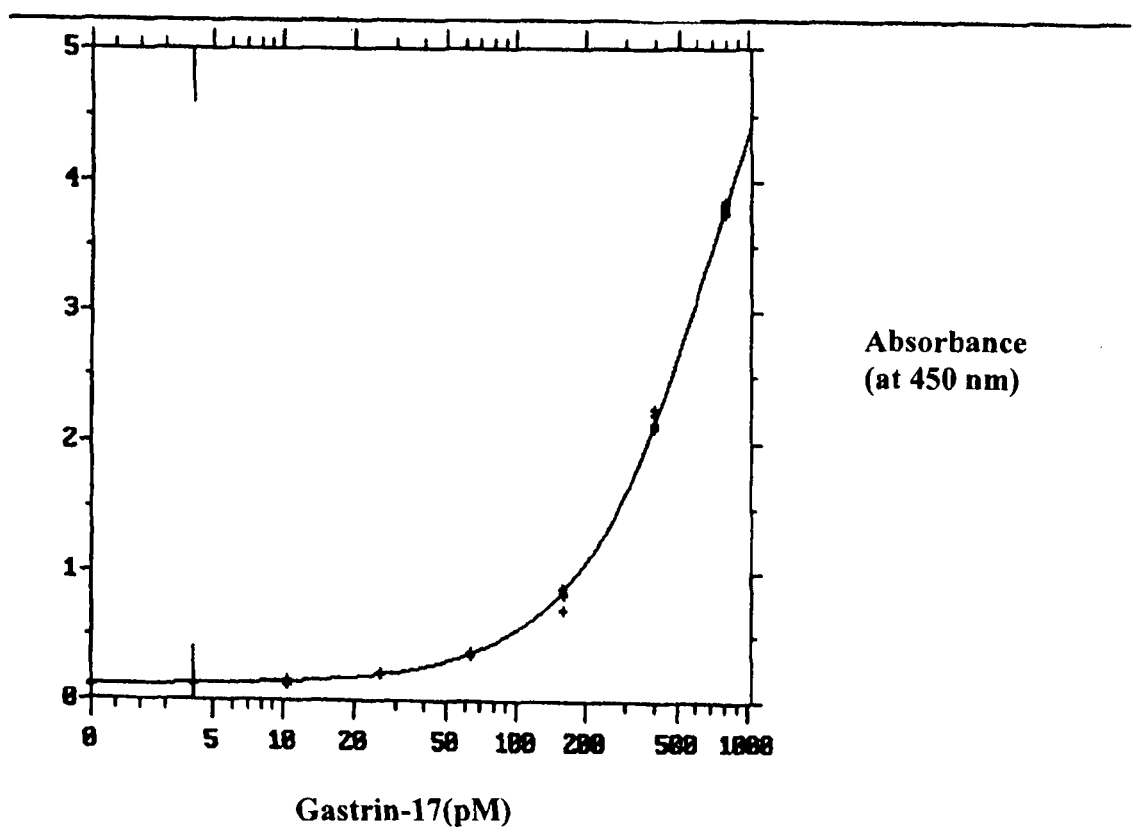
FIG. 1. A representative calibration curve for total gastrin-17 showing gastrin concentration in picomoles plotted against absorbance at 450 nm ($A_{450}$) following the enzyme catalyzed development using tetramethylbenzidine sulfonate (TMBS) as chromogenic substrate.

The following provides the definitions of terms and phrases as used in this specification:

A "gastrin hormone" or "gastrin hormone form" as used interchangeably herein means any biologically active and/or immunologically cross-reactive gastrin hormone peptides. The major forms of gastrin hormone include, but are not limited to gastrin-17 (G17), whether amidated at the C-terminus or having a free C-terminus; glycine extended gastrin-17 (G17-Gly); gastrin-34 (G34), including both the C-terminally amidated form and the form having a free C-terminus; and glycine extended gastrin-34 (G34-Gly).

As used herein, the term "selective" for a particular form of gastrin hormone means that the antibody, while being specific for the particular target epitope of a particular form of gastrin hormone, binds each of the forms of gastrin hormone that contain the target epitope. For instance, the C-terminal of mature (amidated) G17 is common to mature G17 and G34. Thus, a MAb that is specific for the target C-terminal epitope found on mature G17 C-terminus is also selective for G17 (and for G34).

The "total amount" of a gastrin hormone form in a sample as used herein means the sum of the amount of free (unbound) gastrin hormone form plus the amount of complexed (bound) gastrin hormone form. The complexed gastrin may be bound by an antibody or other gastrin-binding moiety in the sample.

A "biological fluid" as used herein means any fluid comprising material of biological origin. Preferred biological fluids for use in the present invention include bodily fluids of an animal, especially a mammal, preferably a human subject. The bodily fluid may be any bodily fluid, including but not limited to blood, plasma, serum, lymph, cerebrospinal fluid (CSF), and the like.

A "preservative agent" as used herein means any agent, supplement or additive that reduces the time dependent degradation of gastrin in a sample of biological fluid, or a liquid sample comprising a biological component. Preservative agents useful in the practice of the present invention include any of the many preservative agents well known in the art, including but not limited to general chemical preservatives, such as for instance, sodium azide, EDTA and protease inhibitors, such as for instance, PMSF (Phenylmethylsulfonylfluoride), and aprotinin (e.g. Trasylol), or a biological preservative, such as for instance, heparin.

A "test plate" as used herein means any solid substrate on which multiple fluid samples may be individually assayed according to the methods of the present invention. A "well" of a test plate as used herein means an area of a test plate used as a sample-receiving location of the plate. Typically, the wells of a test plate are formed from depressions in the surface of the plate sufficient to receive and retain the sample volume plus the volume of any buffer or wash fluid added in any of the steps of the assay procedure.

"Measuring" as applied to a target molecule and as used herein means detecting, quantifying or otherwise determining the amount of an analyte or target molecule.

Specifically, the present invention discloses MAbs that are particularly suitable for use in an immunoenzymometric assay (commonly termed an "ELISA" or enzyme-linked immmunosorbent assay) designed to measure the particular form of gastrin hormone in a biological fluid.

MAbs useful in the practice of the present invention include MAbs that selectively bind the N-terminus of gastrin-17(G17) at an epitope within the amino acid sequence pEG-PWLE (SEQ ID NO: 5).

MAbs useful in the practice of the present invention also include MAbs that selectively bind the C-terminus of gastrin-17 (G17) or gastrin-34 (G34) at an epitope within the amino acid sequence EEAYGWMDF-NH$_2$ (SEQ ID NO: 6).

In another aspect, MAbs useful in the practice of the present invention include MAbs that selectively bind the N-terminus of human gastrin-34 (hG34) at an epitope within the amino acid sequence pELGPQG (SEQ ID NO: 7).

In yet another aspect, MAbs useful in the practice of the present invention include MAbs that selectively bind the C-terminus of glycine-extended gastrin-17 (G17-Gly) and glycine-extended gastrin-34 (G34-Gly) at an epitope within the amino acid sequence YGWMDFG (SEQ ID NO: 8).

MAbs useful in the practice of the present invention preferably bind the gastrin hormone form for which they exhibit selective binding with an association constant ($K_a$) of from about $10^6$ to about $10^7$ $LM^{-1}$, preferably the MAbs bind the gastrin hormone form with a $K_a$ from about $10^7$ to about $10^8$ $LM^{-1}$, yet more preferably from about $10^8$ to about $10^9$ $LM^{-1}$, even more preferably from about $10^9$ to about $10^{10}$ $LM^{-1}$, and still more preferably from about $10^{10}$ to about $10^{11}$ $LM^{-1}$, and most preferably from about $10^{11}$ to about $10^{12}$ $LM^{-1}$ The sample to be analyzed according to the methods of the present invention is preferably a sample of biological fluid from a mammal, the sample containing or being suspected of containing an amount of a peptide to be detected, quantitated or otherwise determined. Preferably, the sample contains gastrin hormone in at least one gastrin hormone form. Most preferably, preservative agent having been added to the sample to form a sample mixture and the sample mixture having been frozen within between about 1-about 15 minutes from sample collection from the mammal.

"Suitable conditions" for binding as used herein means conditions of temperature, pH and ionic strength that permit the binding of antibody to its cognate antigen and the enzyme reaction of the marker enzyme label in a reaction in which an enzyme label is conjugated to an antibody used as a detection agent. Such suitable conditions for antibody-antigen binding and for each type of marker enzyme reaction are well known to those of skill in the art and may be determined specifically for each reaction by routine methods without undue experimentation.

As used herein "detectable marker-conjugated antibody" means any labelled antibody, wherein the label provides a detectable signal, such as for instance an enzyme label, or can be detected with another agent, such as a labelled second antibody that can itself be detected by providing a detectable signal, such as for instance a radioactive label, an enzyme label, a fluorescent or luminescent label or a moiety that can be separately detected such as a biotin label, detectable by an avidin conjugated moiety.

As used herein "detectable marker-conjugated antibody complex" is a complex comprising the antibody to which a detectable marker is conjugated, bound to its cognate antigen, which may be for instance, a gastrin hormone. Such a gastrin hormone-antibody complex provides a detectable signal which can be measured and is directly related to the concentration of detectable antibody. Over the preferred range of concentrations, the signal is directly proportional to the concentration of detectable marker-conjugated antibody complex.

"Development reagent" as used herein means a reagent that is developed by the antibody conjugated enzyme. For instance, the development reagent for alkaline phosphatase can be pNPP.

The invention provides assay methods for measuring total (bound and free) gastrin hormone and methods of evaluating gastrin hormone-blocking treatments. These assay methods are described below. The method of evaluating a gastrin hormone-blocking treatment in a patient is particularly valuable in clinical practice, where timing of decisions to proceed with one therapeutic regimen or another may be critical to the outcome for the patient. The method of the present invention provides information on which to base these critical decisions. The method provides a measure of gastrin hormone prior to or in the early stages of treatment (e.g. shortly after vaccination with a gastrin hormone peptide conjugate vaccine, such as that described in U.S. Pat. No. 5,622,702) and provides one or more measurements of total and/or free gastrin hormone after a period in which the treatment is expected to have begun to be effective.

Analytical Methods

There follows a description of the analytical methods (immunoenzymometric assay) of the invention to determine either total (non-complexed plus antibody-complexed) or free (non-complexed) human gastrin hormone (G17, G17-Gly, G34 or G34-Gly) present in biological fluids such as human plasma, by using monoclonal and/or polyclonal antibodies directed to the C-terminus or the N-terminus of the particular molecular form of gastrin hormone that is being assayed. Alternatively, a combination of a polyclonal antibody directed to the C-terminus or to the N-terminus of the molecule may be used in combination with a monoclonal antibody directed to the N-terminus or to the C-terminus of the molecule respectively.

In the assays described below NUNC Maxisorp, F 96 ELISA plate (cat. No. 439454) test plates were used and the antibody coating solution was prepared in sodium borate buffer (20 mM, pH 8.0, containing 0.1% sodium azide).

1. Plate Coating: Antibody selective for the particular human gastrin molecular form to be tested is coated at an optimal concentration onto the surface of the microwells of a test plate.

Optimal antibody concentration is determined by generating a standard curve using known concentrations of authentic gastrin hormone of the form to be assayed, the standard curve having the required sensitivity and precision over the required useful concentration range. For G17, the useful G17 concentration range of the assay is generally from background (about 4 pM or less) to about 25 pM, or about 50 pM. However, in patients with gastrin-producing tumors, the level of plasma gastrin hormone may be as high as 800 pM or even 1000 pM (1.0 micromolar). The determination of the appropriate sensitivity and precision over the required range can be readily determined by those of ordinary skill in the art without undue experimentation.

2. Plate washing: The coating solution is removed and wash buffer (approx. 400 µl per well) was added and then removed. This wash cycle is repeated as many times as required. Wash buffer was 0.010 M phosphate buffer; 0.0027M potassium chloride and 0.137M sodium chloride, pH 7.4, containing 0.01% w/v Triton X-100). Plate washing may be automated (the Labsystems Wellwash 4 Mk 2, Life Sciences International (UK) Ltd, Basingstoke, UK was used in the assays described below).

3. Plate blocking: Blocking buffer containing protein and detergent (1% BSA/0.1% Triton X-100 in coating buffer) is added to the microwells. Plates may be stored in this form.

4. Sample and standard addition: Plates are washed as described above. Assay buffer (1% BSA, 0.1% bovine γ-globulin and 200 KIU/ml aprotinin prepared in wash buffer) containing rabbit IgG (400 µg/ml), and EDTA (3.4 mM) is added to each well (100 µL/well). Test standards (such as, for instance, gastrin-depleted plasma to which has been added increasing amounts of authentic gastrin hormone) and test plasma samples are added to the wells (20 µL/well). The reaction is allowed to proceed overnight at nominally 4° C. Gastrin depletion of serum samples is readily achieved by allowing the samples to stand at room temperature overnight.

Dissociation peptide G17(1-9) (100 µg/ml) is included in the Assay buffer, rabbit IgG EDTA mix in those assays where total gastrin hormone (including antibody-bound gastrin hormone) is to be assayed.

5. Addition of conjugate: Following washing, assay buffer containing monoclonal or polyclonal antibody specific for the N-terminus of the gastrin hormone form to be assayed, conjugated with an enzyme label, and rabbit IgG (100 µg/ml) is added to each well. The reaction is allowed to proceed at room temperature (nominally +22° C.) with shaking using a microplate shaker. Examples of suitable enzyme substrates for use in development of the detection compound include nitrophenylphosphate for alkaline phosphatase or tetramethylbenzidine sulfonate (TMBS) for horse-radish peroxidase. The degree of color development, sread as Absorbance Units (AU, read at 405 nm in the case of p-nitrophenol, or at 450 nm in the case of TNBS) is indicative of the amount of G17 present in the test sample, and the actual concentration is determined by reading absorbance of the test sample against a standard curve generated with known concentrations of gastrin hormone.

7. Reading: When sufficient assay signal has been obtained the signal is measured, e.g. by a microplate spectrophotometer or fluorimeter.

8. Data Processing: The assay signals obtained with known standard solutions of the gastrin hormone form are used to construct a calibration curve (signal vs. concentration). The calibration curve is used to interpolate concentrations of the gastrin hormone form in test samples.

The specific assay protocols for determining the amounts of total and free gastrin hormone forms are described below:

Determination of Total G17

In this assay, antibody specific for the C-terminus of human gastrin-17 was coated onto the surface of the microwells of the test plate. Plate washing and plate blocking was performed as described for the general method above. Plates were washed as described. Assay buffer containing rabbit IgG (400 µg/ml), dissociation peptide G17$_{(1-9)}$ (100 µg/ml) and EDTA (3.4 mM) was added to each well (100 µL/well). Test standards (gastrin depleted plasma to which 0-4.1-10.2-26.6-64-160-400-1000 pM G17 had been added) and test plasma samples were added to the wells (20 µL/well). The reaction was allowed to proceed overnight in a refrigerator, at nominally 4° C. Following washing, assay buffer containing monoclonal antibody specific for the N-terminus of G17, conjugated with alkaline phosphatase, and rabbit IgG (100 µg/ml) was added to each well. Following washing, chromogenic substrate (pNPP) was added, the plates were incubated and allowed to develop color and read in a plate reader as described above. The assay signals obtained with known standard G17 solutions were used to construct a calibration curve (signal vs. concentration). This calibration curve was used to interpolate G17 concentrations in test samples. A representative calibration curve is shown in FIG. 1.

Determination of Free G17

Figure 2:
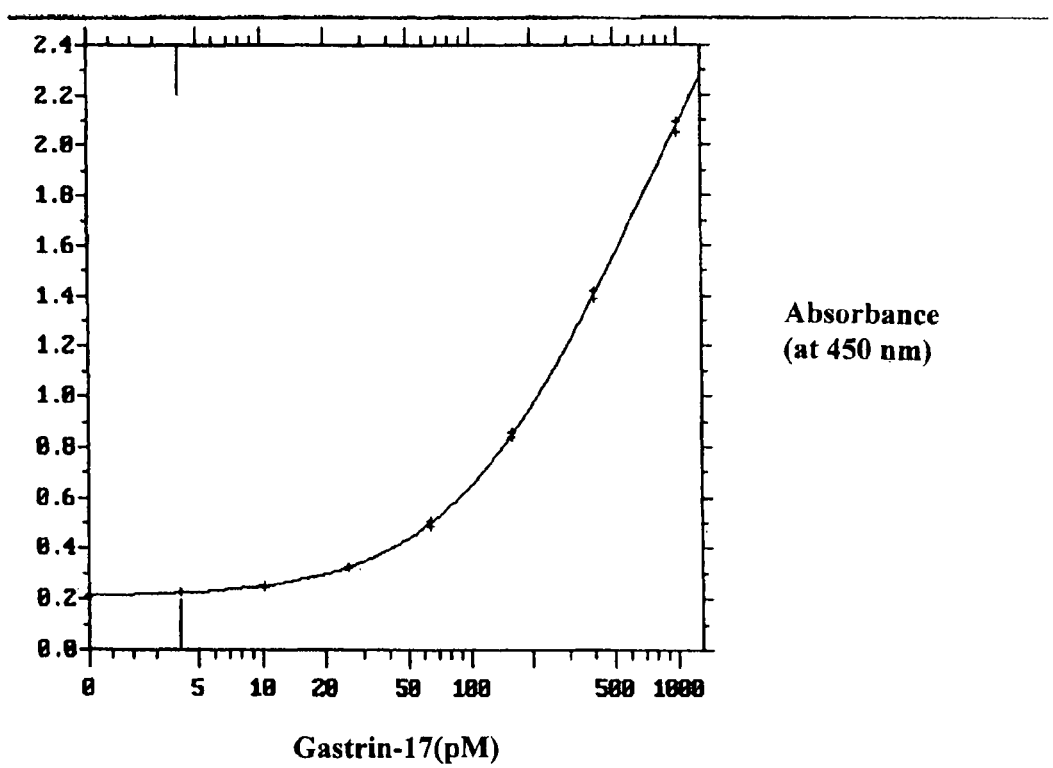
FIG. 2. A representative calibration curve for free gastrin-17 showing gastrin concentration in picomoles plotted against absorbance at 450 nm ($A_{450}$) as above.

Antibody specific for the N-terminus of the human gastrin-17 molecule was coated onto the surface of the microwells of a test plate. Plate washing and plate blocking was performed as described for the general method above. Plates were washed as described. Assay buffer (1% BSA, 0.1% bovine γ-globulin and 200 KIU/ml aprotinin prepared in wash buffer) containing rabbit IgG (400 μg/ml) was added and the reaction allowed to proceed at room temperature (nominally +22° C.), with shaking using a microplate shaker. Following washing, assay buffer containing monoclonal antibody specific for the C-terminus of G17, conjugated with alkaline phosphatase as enzyme label, and rabbit IgG (100 μg/ml) was added to each well. The reaction was allowed to proceed at room temperature (nominally +22° C.) with shaking using a microplate shaker. Following washing, chromogenic substrate (pNPP) was added, the plates were incubated and allowed to develop color and read in a plate reader as described above. The assay signals obtained with known standard G17 solutions were used to construct a calibration curve (signal vs. concentration) as in the assay for total G17 described above. The calibration curve was used to interpolate G17 concentrations in test samples. A representative calibration curve is shown in FIG. 2.

Determination of Total G17-Gly

Antibody specific for the C-terminus of the human glycine-extended gastrin-17 molecule was coated onto the surface of the microwells of a test plate as described above. Plate washing and plate blocking was performed as described for the general method above. Plates were washed as described. Assay buffer (1% BSA, 0.1% bovine γ-globulin and 200 KIU/ml aprotinin prepared in wash buffer) containing rabbit IgG (400 μg/ml), dissociation peptide $G17_{(1-9)}$ (100 μg/ml) and EDTA (3.4 mM) was added to each well (e.g. 100 μL/well). Test standards (gastrin depleted plasma to which had been added G17-gly at 0-4.1-10.2-26.6-64-160-400-1000 pM G17-Gly) and test plasma samples were added to the wells (e.g. 20 μL/well). The reaction was allowed to proceed overnight at nominally 4° C. Subsequent steps were exactly as described above for the assay for total G17.

Determination of Free G17-Gly

Antibody specific for the N-terminus of the G17-Gly molecule was coated onto the surface of the microwells of a test plate. Plate washing and plate blocking was performed as described for the general method above. Plates were washed as described. Assay buffer (1% BSA, 0.1% bovine γ-globulin and 200 KIU/ml aprotinin prepared in wash buffer) containing rabbit IgG (400 μg/ml) was added (e.g. 100 μL/well), followed by sample/standard (e.g. 50 μL/well) and the reaction allowed to proceed at room temperature (nominally +22° C.), with shaking using a microplate shaker. Following washing, assay buffer containing monoclonal antibody specific for the C-terminus of G17-Gly, conjugated with alkaline phosphatase, and rabbit IgG (100 μg/ml) was added to each well. The reaction was allowed to proceed at room temperature (nominally +22° C.) with shaking using a microplate shaker. Subsequent steps were exactly as described above for the assay for free G17.

Determination of G34

Antibody specific for the N-terminus of the human gastrin-34 was coated onto the surface of the microwells of a test plate. Plate washing and plate blocking was performed as described for the general method above. Plates were washed as described. Assay buffer (1% BSA, 0.1% bovine γ-globulin and 200 KIU/ml aprotinin prepared in wash buffer) containing rabbit IgG (400 μg/ml) was added (e.g. 100 μl/well), followed by sample/standard (e.g. 50 μl/well). The reaction was allowed to proceed at room temperature (nominally +22° C.), with shaking using a microplate shaker. Following washing, assay buffer containing monoclonal antibody specific for the C-terminus of G34, conjugated with alkaline phosphatase, and rabbit IgG (100 μg/ml) was added to each well and the reaction allowed to proceed at room temperature (nominally +22° C.) with shaking using a microplate shaker. Addition of the chromogenic substrate pNPP and reading of sample signal in the plate wells using a plate reader, and subsequent data processing was as described above. The assay signals obtained with known standard G34 solutions are used to construct a calibration curve (signal vs. concentration). The calibration curve is used to interpolate G34 concentrations in test samples.

EXAMPLES

Example 1

Determination of Total Gastrin 17 in Gastrin-Depleted Serum Samples to which Known Amounts of Gastrin 17 Had been Added Serum was depleted of gastrin hormone by standing at room temperature overnight to allow endogenous proteases to completely degrade the gastrin hormone present.

To determine intra-assay precision and accuracy, known amounts of authentic gastrin 17 (G17) were added to replicate aliquots of the gastrin-depleted serum sample to achieve the nominal concentrations shown in Table 1. The assay for total G17 was performed using the N-terminal gastrin peptide in the same procedure as for serum samples containing anti-gastrin hormone antibody. The N-terminal gastrin peptide G17(1-9) was added at the steps of sample and standard addition as described above at a concentration of 100 μg/ml. The results, provided in Table 1, show that the assay accurately quantitated G17 within the accepted limits of ELISA methods, said ELISA limits being ±20% relative error. More importantly, the assay is most accurate at the concentrations of G17 at and below 100 pM, which (as noted above) are the concentrations normally found in patients.

TABLE 1

| | Total Gastrin 17 assay Gastrin 17 concentration (pM) | | | | |
| --- | --- | --- | --- | --- | --- |
| | 7.50 | 15.00 | 100.0 | 600.0 | 720.0 |
| mean | 7.5 | 14.3 | 99.3 | 717.1 | 814.1 |
| sd | 0.8 | 0.9 | 1.7 | 16.2 | 7.7 |
| CV % | 11.2 | 6.5 | 1.7 | 2.3 | 0.9 |
| RE % | 0.0 | −4.7 | −0.7 | 19.5 | 13.1 | n = 6 Six replicate samples were assayed
sd Standard deviation
CV Coefficient of variation (calculated before rounding)
RE Relative error (calculated after rounding)

Example 2

Determination of Free Gastrin 17 in Gastrin-Depleted Serum Samples to which Known Amounts of Gastrin 17 Had been Added This assay was performed according to the method described in the "Assay Procedure" above for the determination of free gastrin-17 (G17). The results, provided in Table 2, show that the assay accurately quantitated free G17 within the accepted limits of ELISA methods. More importantly, the assay is most accurate at the concentrations of G17 at and below 100 pM, which are the concentrations normally found in patients.

TABLE 2

Free gastrin 17 assay
Inter-assay precision and accuracy data

| | Free gastrin 17 concentration (pM) | | | | |
|---|---|---|---|---|---|
| | 7.50 | 15.00 | 100.0 | 600.0 | 900.0 |
| mean | 7.55 | 13.41 | 94.01 | 556.6 | 892.8 |
| sd | 1.67 | 1.26 | 5.47 | 43.01 | 112.1 |
| CV % | 22.2 | 9.4 | 5.8 | 7.7 | 12.6 |
| RE % | 0.7 | −10.6 | −6.0 | −7.2 | −0.8 | n = 9 Nine replicate samples were assayed
sd Standard deviation
CV Coefficient of variation (calculated before rounding)
RE Relative error (calculated after rounding)

Example 3

Gastrin-17 Stability

The stability of Gastrin at room temperature (about 22° C.) was assessed by the total gastrin assay as described above by measuring total G17 immediately after sample preparation (0 hour sample) to achieve known G17 concentrations of 15, 100 and 600 pM, and after 2 hours at room temperature on the bench. The results, demonstrating a substantial decrease in G17 concentration in each of the samples, are shown in Table 3, below. This demonstrates the importance of proper sample handling techniques, including minimal exposure to elevated temperatures when plasma is prepared from a sample of patients blood, to the accuracy of gastrin values obtained using the assay methods of the invention to test samples for gastrin hormone.

TABLE 3

Total Gastrin 17 assay
Stability of gastrin 17 in human plasma at room temperature (ca 22° C.)

| | | Measured gastrin 17 concentration (pM) | | |
|---|---|---|---|---|
| | | 15 | 100 | 600 |
| 0[a] hours | mean | 11.6 | 89.4 | 605.5 |
| | sd | 2.8 | 4.3 | 25.0 |
| | CV (%) | 23.8 | 4.8 | 4.1 |
| | RE (%) | −22.7 | −10.6 | 0.9 |
| 2 hours | mean | 5.5 | 59.1 | 400.5 |
| | sd | 3.1 | 2.0 | 19.7 |
| | CV (%) | 55.2 | 3.5 | 4.9 |
| | RE (%) | −63.3 | −40.9 | −33.3 |

[a]Mean result used as baseline
sd Standard deviation
CV Coefficient of variation (calculated before rounding)
RE Relative error (calculated after rounding)

Incorporation by Reference

All of the patents and publications cited in this specification are hereby expressly incorporated by reference in their entireties.

Deposit of Hybridoma Cell Lines

The following hybridomas that produce particular MAbs of the present invention were deposited with the American Type Culture Collection (ATCC, Manassas, Va.) on Mar. 25, 2004:

1. Hybridoma 400-1 produces MAb 400-1 that selectively binds an N-terminal epitope of G17 or Gly-extended G17 and is assigned accession number PTA-5889.
2. Hybridoma 400-2 produces MAb 400-2 that selectively binds an N-terminal epitope of G17 or Gly-extended G17 and is assigned accession number PTA-5890.
3. Hybridoma 400-3 produces MAb 400-3 that selectively binds an N-terminal epitope of G17 or Gly-extended G17 and is assigned accession number PTA-5891.
4. Hybridoma 400-4 produces MAb 400-4 that selectively binds an N-terminal epitope of G17 or Gly-extended G17 and is assigned accession number PTA-5892.
5. Hybridoma 401-2 produces MAb 401-2 that selectively binds an N-terminal epitope of G34 or Glycine-extended G34 and is assigned accession number PTA-5893.
6. Hybridoma 445-1 produces MAb 445-1 that selectively binds a C-terminal epitope of Glycine-extended G17 or Glycine-extended G34 and is assigned accession number PTA-5894.
7. Hybridoma 445-2 produces MAb 445-2 that selectively binds a C-terminal epitope of Glycine-extended G17 or Glycine-extended G34 and is assigned accession number PTA-5895.
8. Hybridoma 458-1 produces MAb 458-1 that selectively binds a C-terminal epitope of G17 or G34 and is assigned accession number PTA-5896.

What is claimed is:

1. A method for determining the total amount of gastrin hormone in a biological fluid sample, comprising the steps of:
   (a) obtaining a biological fluid sample comprising gastrin hormone from a patient;
   (b) providing an immobilized antibody that selectively binds a C-terminal epitope of the gastrin hormone;
   (c) incubating the sample in the presence of an N-terminal sequence gastrin peptide under suitable conditions for binding of the gastrin hormone in the sample to said antibody to produce an immobilized complex of said antibody bound to the gastrin hormone;
   (d) washing the immobilized complex to remove N-terminal sequence gastrin peptide, and incubating the complex with a suitable detectable marker-conjugated antibody that selectively binds an N-terminal epitope of gastrin hormone to form an immobilized detectable marker-conjugated antibody complex;
   (e) washing the immobilized detectable marker-conjugated antibody complex, and incubating with a development reagent; and
   (f) measuring the developed reagent to determine the total amount of the gastrin hormone in the biological fluid sample;
wherein the immobilized antibody that selectively binds a C-terminal epitope of the gastrin hormone is a monoclonal antibody selected from the monoclonal antibody produced by hybridoma 458-1 (ATCC accession no. PTA-5896), the monoclonal antibody produced by hybridoma 445-1 (ATCC accession no. PTA-5894) and the monoclonal antibody produced by hybridoma 445-2 (ATCC accession no. PTA-5895).

2. The method of claim 1, wherein the C-terminal selective antibody is the monoclonal antibody produced by the hybridoma designated 458-1 and deposited under ATCC accession no. PTA-5896.

3. The method of claim 1, wherein the N-terminal selective antibody is selective for the N-terminal of G17.

4. The method of claim 3, wherein the N-terminal selective antibody is a monoclonal antibody.

5. The method of claim 4, wherein the N-terminal selective antibody is the monoclonal antibody produced by a hybridoma selected from the group consisting of the hybridoma designated 400-1 and deposited under ATCC accession no. PTA-5889, the hybridoma designated 400-2 and deposited under ATCC accession no. PTA-5890, the hybridoma designated 400-3 and deposited under ATCC accession no. PTA-5891 and the hybridoma designated 400-4 and deposited under ATCC accession no. PTA-5892.

6. The method of claim 1, wherein the N-terminal selective antibody is selective for the N-terminal of G34.

7. The method of claim 6, wherein the N-terminal selective antibody is a monoclonal antibody.

8. The method of claim 7, wherein the N-terminal selective antibody is the monoclonal antibody produced by the hybridoma designated 401-2 and deposited under ATCC accession no. PTA-5893.

9. The method of claim 1, wherein the C-terminal selective antibody is the monoclonal antibody produced by a hybridoma selected from the group consisting of the hybridoma designated 445-1 and deposited under ATCC accession no. PTA-5894 and the hybridoma designated 445-2 and deposited under ATCC accession no. PTA-5895.

* * * * *